US012042143B2

(12) United States Patent
Parker et al.

(10) Patent No.: US 12,042,143 B2
(45) Date of Patent: Jul. 23, 2024

(54) DEVICES AND METHODS FOR PASSING AND RETRIEVING SUTURE THROUGH TISSUE

(71) Applicant: Stryker Corporation, Kalamazoo, MI (US)

(72) Inventors: John Parker, San Jose, CA (US); Roger Pisarnwongs, Santa Clarita, CA (US); Jessica Kwong, Lomita, CA (US); Jamie Anderson, Denver, CO (US)

(73) Assignee: Stryker Corporation, Kalamazoo, MI (US)

( * ) Notice: Subject to any disclaimer, the term of this patent is extended or adjusted under 35 U.S.C. 154(b) by 125 days.

(21) Appl. No.: 17/651,570

(22) Filed: Feb. 17, 2022

(65) Prior Publication Data

US 2022/0265267 A1    Aug. 25, 2022

Related U.S. Application Data

(60) Provisional application No. 63/153,859, filed on Feb. 25, 2021.

(51) Int. Cl.
*A61B 17/04*    (2006.01)
(52) U.S. Cl.
CPC .................. *A61B 17/0491* (2013.01)
(58) Field of Classification Search
CPC ............ A61B 17/0491; A61B 17/0485; A61B 17/0469; A61B 17/0483
See application file for complete search history.

(56) References Cited

U.S. PATENT DOCUMENTS

| 1,037,864 A | 9/1912 | Carlson et al. |
| 1,449,087 A | 3/1923 | Bugbee |

(Continued)

FOREIGN PATENT DOCUMENTS

| EP | 1703846 B1 | 4/2013 |
| WO | 95/25468 A1 | 9/1995 |

(Continued)

OTHER PUBLICATIONS

Decision to Grant dated Jun. 1, 2017, directed to EP Application No. 10 800 336.9; 2 pages.

(Continued)

*Primary Examiner* — Tuan V Nguyen
(74) *Attorney, Agent, or Firm* — Morrison & Foerster LLP

(57) ABSTRACT

A suture passer includes a first shaft comprising a hollow tube and a distal portion located distally of a distal end of the hollow tube; a needle comprising a needle tip and a needle shaft translatably mounted in the hollow tube for passing a suture loaded holder through tissue positioned between the distal end of the hollow tube and the distal portion of the first shaft; an actuatable engagement located in the distal portion of the first shaft for retaining the suture loaded holder after the suture loaded holder has passed through the tissue; a sheath extending around an exterior of the needle shaft and translatable with the needle shaft for at least a portion of a stroke of the needle, wherein the sheath is moveable relative to the needle for actuating the engagement to an unlatched position to release the holder from the distal portion of the first shaft.

46 Claims, 18 Drawing Sheets

(56) References Cited

U.S. PATENT DOCUMENTS

| | | | |
|---|---|---|---|
| 1,635,066 A | 7/1927 | Wells | |
| 1,815,725 A | 7/1931 | Pilling et al. | |
| 1,822,330 A | 9/1931 | Ainslie | |
| 1,856,721 A | 5/1932 | Nagelmann | |
| 2,457,379 A | 12/1948 | Kallenbach | |
| 2,579,192 A | 12/1951 | Kohl | |
| 2,738,790 A | 3/1956 | Todt, Sr. et al. | |
| 2,813,736 A | 11/1957 | Archer et al. | |
| 2,959,172 A | 11/1960 | Held | |
| 3,470,875 A | 10/1969 | Johnson | |
| 3,842,840 A | 10/1974 | Schweizer | |
| 3,901,244 A | 8/1975 | Schweizer | |
| 3,946,740 A | 3/1976 | Bassett | |
| 4,164,225 A | 8/1979 | Johnson et al. | |
| 4,224,947 A | 9/1980 | Fukuda | |
| 4,312,337 A | 1/1982 | Donohue | |
| 4,373,530 A | 2/1983 | Kilejian | |
| 4,596,249 A | 6/1986 | Freda et al. | |
| 4,602,635 A | 7/1986 | Mulhollan et al. | |
| 4,712,545 A | 12/1987 | Honkanen | |
| 4,759,364 A | 7/1988 | Boebel | |
| 4,836,205 A | 6/1989 | Barrett | |
| 4,890,615 A | 1/1990 | Caspari et al. | |
| 4,923,461 A | 5/1990 | Caspari et al. | |
| 5,059,201 A | 10/1991 | Asnis | |
| 5,281,237 A | 1/1994 | Gimpelson | |
| 5,312,422 A | 5/1994 | Trott | |
| 5,312,423 A | 5/1994 | Rosenbluth et al. | |
| 5,336,229 A | 8/1994 | Noda | |
| 5,364,410 A | 11/1994 | Failla et al. | |
| 5,376,096 A | 12/1994 | Foster | |
| 5,387,227 A | 2/1995 | Grice | |
| 5,389,103 A | 2/1995 | Melzer et al. | |
| 5,499,991 A | 3/1996 | Garman et al. | |
| 5,507,754 A | 4/1996 | Green et al. | |
| 5,569,269 A | 10/1996 | Hart et al. | |
| 5,618,290 A | 4/1997 | Toy et al. | |
| 5,643,292 A | 7/1997 | Hart | |
| 5,649,939 A | 7/1997 | Reddick | |
| 5,746,753 A | 5/1998 | Sullivan et al. | |
| 5,792,153 A | 8/1998 | Swain et al. | |
| 5,890,538 A | 4/1999 | Beirute et al. | |
| 5,904,692 A | 5/1999 | Steckel et al. | |
| 5,980,538 A | 11/1999 | Fuchs et al. | |
| 5,993,466 A | 11/1999 | Yoon | |
| 6,117,144 A | 9/2000 | Nobles et al. | |
| 6,443,963 B1 | 9/2002 | Baldwin et al. | |
| 6,517,552 B1 | 2/2003 | Nord et al. | |
| 6,551,330 B1 | 4/2003 | Bain et al. | |
| 6,770,084 B1 | 8/2004 | Bain et al. | |
| 6,893,448 B2 | 5/2005 | O'Quinn et al. | |
| 6,936,054 B2 | 8/2005 | Chu | |
| 7,083,628 B2 | 8/2006 | Bachman | |
| 7,118,583 B2 | 10/2006 | O'Quinn et al. | |
| 7,211,093 B2 | 5/2007 | Sauer et al. | |
| 7,377,926 B2 | 5/2008 | Topper et al. | |
| 7,407,505 B2 | 8/2008 | Sauer et al. | |
| 7,544,199 B2 | 6/2009 | Bain et al. | |
| 7,608,084 B2 | 10/2009 | Oren et al. | |
| 7,815,654 B2 | 10/2010 | Chu | |
| 7,879,048 B2 | 2/2011 | Bain et al. | |
| 8,172,857 B2 | 5/2012 | Fogel | |
| 8,361,089 B2 | 1/2013 | Chu | |
| 8,469,974 B2 | 6/2013 | Skinlo et al. | |
| 8,764,771 B2 | 7/2014 | Chu | |
| 8,906,041 B2 | 12/2014 | Chu | |
| 9,149,270 B2 | 10/2015 | Fogel | |
| 9,198,655 B2 | 12/2015 | Skinlo et al. | |
| 9,271,719 B2 | 3/2016 | Skinlo et al. | |
| 10,278,690 B2 | 5/2019 | Skinlo et al. | |
| 10,357,243 B2 | 7/2019 | Skinlo | |
| 2002/0116067 A1 | 8/2002 | Mears et al. | |
| 2005/0090827 A1 | 4/2005 | Gedebou | |
| 2005/0222589 A1 | 10/2005 | Chu | |
| 2005/0251153 A1 | 11/2005 | Sakamoto et al. | |
| 2006/0282094 A1 | 12/2006 | Stokes et al. | |
| 2007/0213833 A1 | 9/2007 | Mears et al. | |
| 2007/0270885 A1 | 11/2007 | Weinert et al. | |
| 2008/0077162 A1 | 3/2008 | Domingo | |
| 2009/0062819 A1 | 3/2009 | Burkhart et al. | |
| 2009/0069846 A1 | 3/2009 | Bull et al. | |
| 2009/0131956 A1 | 5/2009 | Dewey et al. | |
| 2010/0121348 A1 | 5/2010 | van der Burg et al. | |
| 2010/0121352 A1 | 5/2010 | Murray et al. | |
| 2010/0256657 A1 | 10/2010 | Domingo | |
| 2011/0028998 A1 | 2/2011 | Adams et al. | |
| 2011/0060352 A1 | 3/2011 | Chu | |
| 2011/0066165 A1 | 3/2011 | Skinlo et al. | |
| 2011/0118758 A1* | 5/2011 | Sauer .............. A61B 17/0482 606/144 |
| 2011/0144442 A1 | 6/2011 | Farrell et al. | |
| 2011/0276064 A1* | 11/2011 | Henrichsen ........ A61B 17/0469 606/145 |
| 2012/0215235 A1 | 8/2012 | Fogel | |
| 2013/0041387 A1 | 2/2013 | Skinlo et al. | |
| 2013/0103056 A1 | 4/2013 | Chu | |
| 2013/0231669 A1 | 9/2013 | Sinnott et al. | |
| 2014/0171980 A1 | 6/2014 | Skinlo et al. | |
| 2014/0180313 A1* | 6/2014 | Harrison ............ A61B 17/0469 606/148 |
| 2016/0249906 A1 | 9/2016 | Skinlo et al. | |
| 2016/0338691 A1 | 11/2016 | Weber et al. | |
| 2017/0014123 A1 | 1/2017 | Skinlo et al. | |
| 2019/0365379 A1 | 12/2019 | Harrison et al. | |
| 2020/0046341 A1 | 2/2020 | Skinlo et al. | |
| 2023/0093590 A1 | 3/2023 | Skinlo et al. | |

FOREIGN PATENT DOCUMENTS

| | | |
|---|---|---|
| WO | 02/24078 A1 | 3/2002 |
| WO | 2008/130656 A1 | 10/2008 |

OTHER PUBLICATIONS

Extended European Search Report dated Mar. 6, 2015, directed to EP Application No. 10 800 336.9; 5 pages.

Intention to Grant dated Jan. 13, 2017, directed to EP Application No. 10 800 336.9; 5 pages.

International Preliminary Report on Patentability dated Aug. 29, 2023, directed to International Application No. PCT/US2022/016821; 9 pages.

International Preliminary Report on Patentability dated Jan. 17, 2012, directed to International Application No. PCT/US2010/041230; 8 pages.

International Search Report and Written Opinion mailed May 27, 2022, directed to International Application No. PCT/US2022/016821; 17 pages.

International Search Report and Written Opinion mailed Sep. 7, 2010, directed to International Application No. PCT/US2010/041230; 10 pages.

Notice of Acceptance dated Sep. 22, 2015, directed to AU Application No. 2010273677; 2 pages.

Notice of Allowance dated Mar. 8, 2019, directed to CA Application No. 2,767,713; 1 page.

Office Action dated Apr. 18, 2016, directed to EP Application No. 10 800 336.9; 4 pages.

Office Action dated Aug. 22, 2016, directed to CA Application No. 2,767,713; 5 pages.

Office Action dated Jan. 26, 2018, directed to CA Application No. 2,767,713; 3 pages.

Office Action dated Jul. 4, 2017, directed to CA Application No. 2,767,713; 3 pages.

Office Action dated Oct. 30, 2018, directed to CA Application No. 2767713; 5 pages.

Patent Examination Report No. 1 issued Mar. 18, 2014, directed to AU Application No. 2010273677; 4 pages.

Patent Examination Report No. 2 issued Mar. 19, 2015, directed to AU Application No. 2010273677; 4 pages.

(56) References Cited

OTHER PUBLICATIONS

Skinlo et al., Office Action mailed Feb. 23, 2018, directed to U.S. Appl. No. 14/955,451; 13 pages.
Skinlo et al., Office Action mailed Jul. 26, 2018, directed to U.S. Appl. No. 14/955,451; 12 pages.
Skinlo et al., Office Action mailed Oct. 14, 2014, directed to U.S. Appl. No. 13/564,087; 26 pages.
Skinlo et al., U.S. Corrected Notice of Allowability mailed Jan. 28, 2019, directed to U.S. Appl. No. 15/048,000; 6 pages.
Skinlo et al., U.S. Notice of Allowance and Fee(s) Due mailed Dec. 11, 2015, directed to U.S. Appl. No. 13/925,242; 17 pages.
Skinlo et al., U.S. Notice of Allowance and Fee(s) due mailed Dec. 27, 2018, directed to U.S. Appl. No. 15/048,000; 11 pages.
Skinlo et al., U.S. Notice of Allowance and Fee(s) Due mailed Jul. 15, 2022, directed to U.S. Appl. No. 16/515,407; 12 pages.
Skinlo et al., U.S. Notice of Allowance and Fee(s) Due mailed Jul. 17, 2015, directed to U.S. Appl. No. 13/564,087; 12 pages.
Skinlo et al., U.S. Notice of Allowance and Fee(s) due mailed Mar. 25, 2019, directed to U.S. Appl. No. 14/955,451; 9 pages.
Skinlo et al., U.S. Notice of Allowance and Fee(s) due mailed Mar. 4, 2013, directed to U.S. Appl. No. 12/831,937; 10 pages.
Skinlo et al., U.S. Office Action dated Dec. 24, 2021, directed to U.S. Appl. No. 16/515,407; 9 pages.
Skinlo et al., U.S. Office Action dated Jan. 12, 2024, directed to U.S. Appl. No. 18/059,425; 13 pages.
Skinlo et al., U.S. Office Action mailed Apr. 29, 2015, directed to U.S. Appl. No. 13/925,242; 15 pages.
Skinlo et al., U.S. Office Action mailed Jul. 31, 2014, directed to U.S. Appl. No. 13/925,242; 19 pages.
Skinlo et al., U.S. Office Action mailed May 22, 2018, directed to U.S. Appl. No. 15/048,000; 13 pages.
Skinlo et al., U.S. Office Action mailed Sep. 4, 2012, directed to U.S. Appl. No. 12/831,937; 22 pages.
Skinlo et al., U.S. Restriction Requirement dated Aug. 27, 2021, directed to U.S. Appl. No. 16/515,407; 7 pages.
Skinlo et al., U.S. Restriction Requirement dated May 19, 2014, directed to U.S. Appl. No. 13/564,087; 11 pages.
Skinlo et al., U.S. Restriction Requirement dated Jun. 1, 2012, directed to U.S. Appl. No. 12/831,937; 10 pages.
Skinlo et al., U.S. Restriction Requirement dated Nov. 22, 2017, directed to U.S. Appl. No. 14/955,451; 10 pages.

* cited by examiner

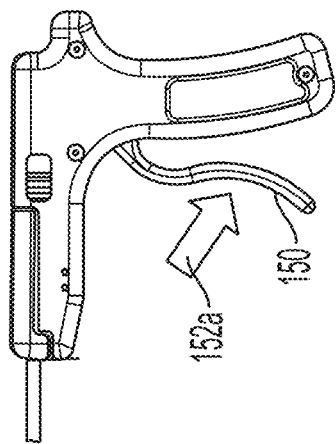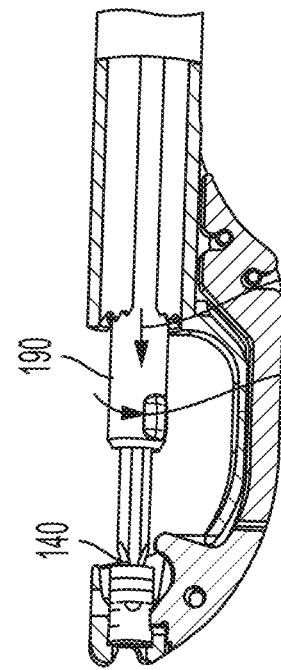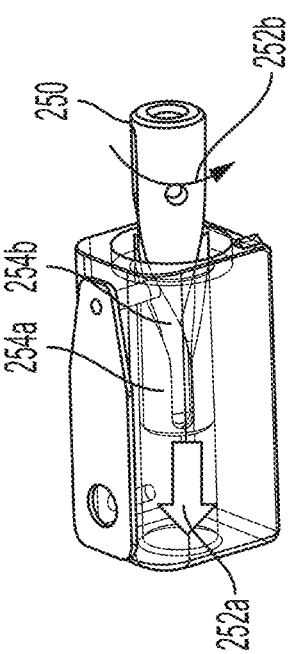

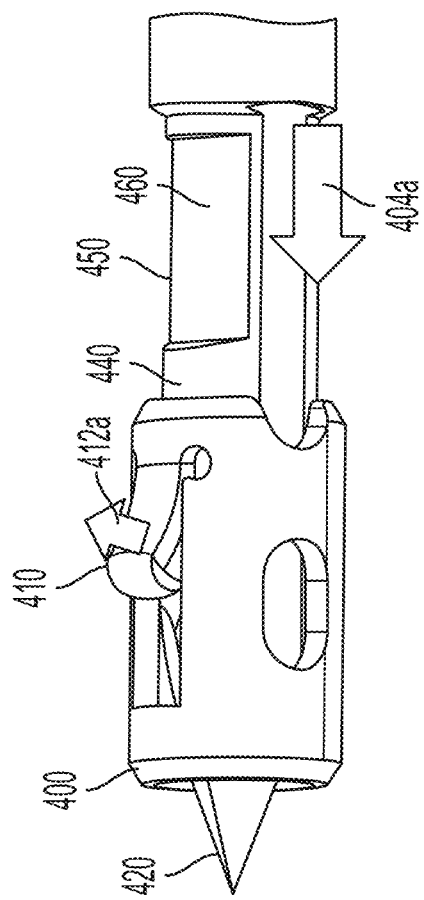
FIG. 9B
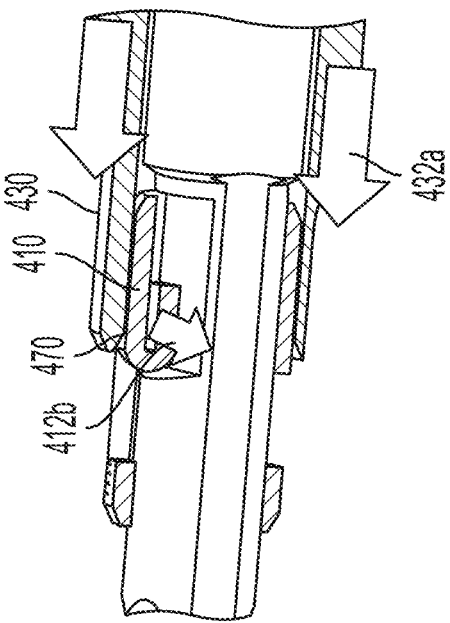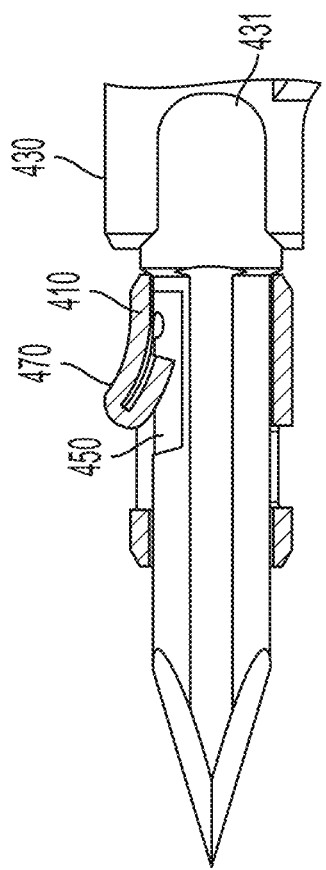
FIG. 9D
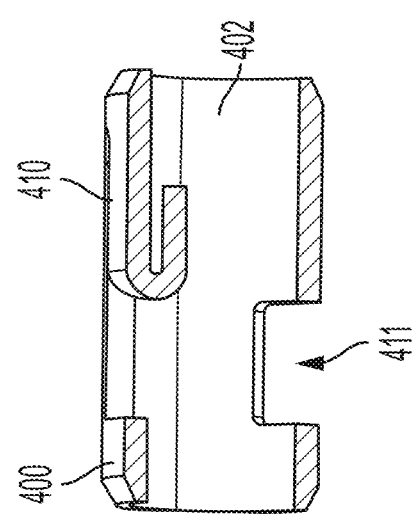
FIG. 9A
FIG. 9C

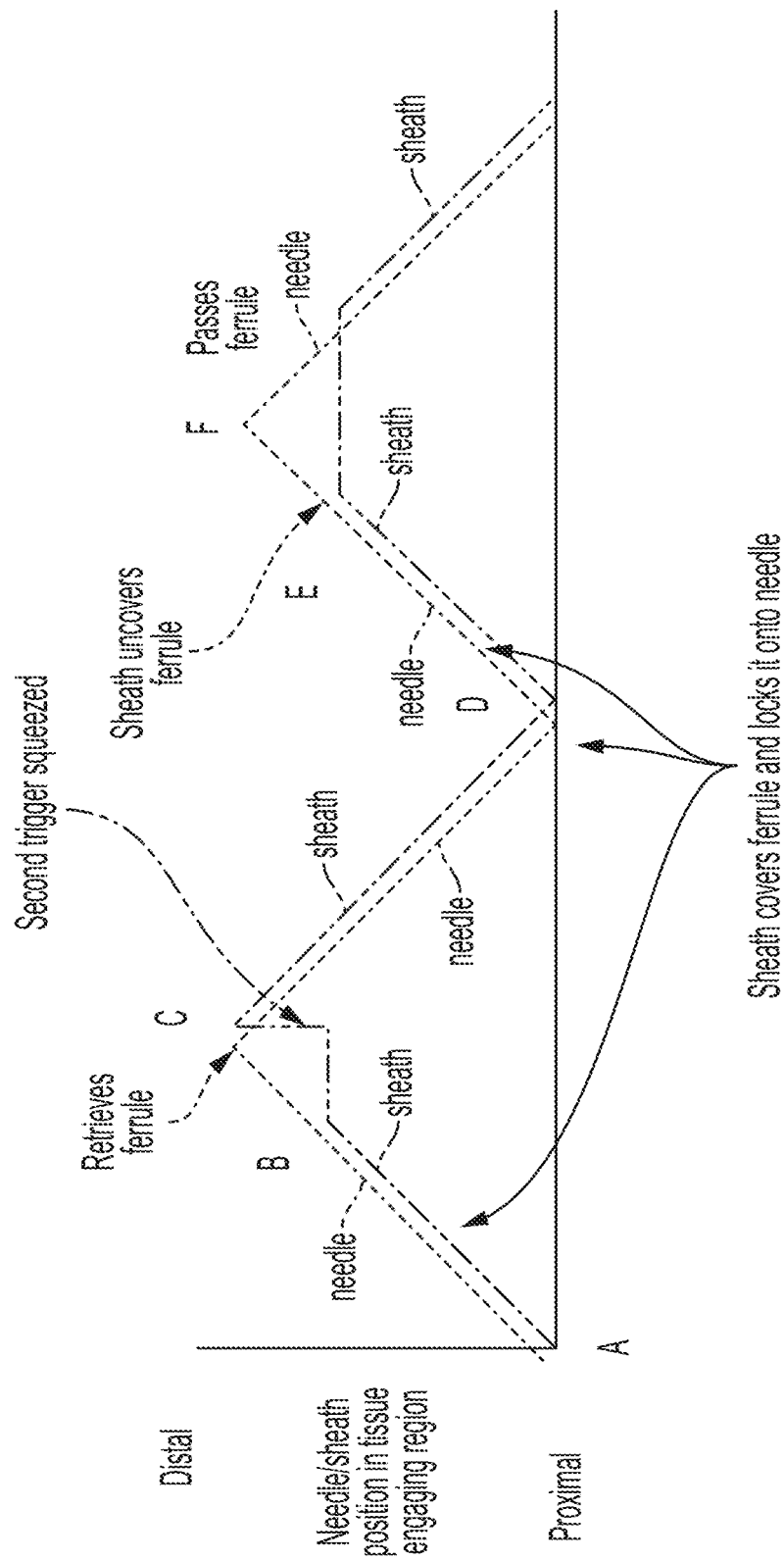

DEVICES AND METHODS FOR PASSING AND RETRIEVING SUTURE THROUGH TISSUE

CROSS-REFERENCE TO RELATED APPLICATIONS

This application claims the benefit of U.S. Provisional Application No. 63/153,859, filed Feb. 25, 2021, the entire contents of which are hereby incorporated by reference herein.

FIELD

This disclosure generally relates to surgical devices and procedures, and more specifically to surgical devices and procedures for passing and retrieving suture through tissue.

BACKGROUND

Suturing of tissue generally involves mounting suture to a needle, piercing the tissue with the suture-loaded needle, and passing the suture-loaded needle through the tissue. Multiple passes of the suture through the tissue are typically used to stitch the tissue together. Minimally invasive surgical procedures that involve suturing require the surgeon to pass the suture through the tissue using one or more tools inserted into the surgical cavity through small incisions and, thus, suturing during minimally invasive surgery can be challenging. Suture passers are tools that can be used during minimally invasive surgeries to pass suture through tissue within the surgical cavity. For example, suture passers loaded with suture may be positioned in the surgical cavity and used to complete a first pass of suture through tissue in the surgical cavity. Typically, after the first pass of suture through tissue, the suture passer is removed from the surgical cavity to reload the conventional suture passer with suture. Once reloaded with suture outside of the surgical cavity, the suture passer is repositioned back in the surgical cavity and then used to complete the second pass of suture through tissue. Such a reloading process, as described above, is cumbersome as it involves moving the suture passer in and out of the surgical site and also manually (for example, by hand) picking up the passed suture to reload the suture passer to stitch tissue.

SUMMARY

According to an aspect, a suture passer is configured to repeatedly pass and retrieve a suture-loaded holder through tissue for continuous suturing without requiring the suture-loaded holder to be removed from the surgical cavity. The suture passer may include a tissue engaging recess that may be positioned around tissue to be sutured in the surgical cavity. The suture-loaded holder may be mounted on a moveable needle of the suture passer and passed through tissue positioned in the tissue engaging recess via distal movement of the needle. After passing distally through the tissue, the suture-loaded holder may be retained in a distal portion of the suture passer and may unmount from the needle as the needle retracts back through tissue away from the distal portion. The suture-loaded holder may be retained in the distal portion by a component of the suture passer in the distal portion that engages the suture-loaded holder. The suture passer may be repositioned on the tissue and the needle may then pass through a different portion of tissue to the distal portion and pick up the suture-loaded holder retained in the distal portion. For the needle to pick up the suture-loaded holder from the distal portion, a sheath of the suture passer which moves along with the needle to the distal portion, may move relative to the needle in the distal portion and thus releases the suture holder from the distal portion. After picking up the suture-loaded holder, the needle may then retract the suture-loaded holder back through tissue and away from the distal portion as the needle retracts once again away from the distal portion. The passing of the suture-loaded holder to the distal portion and picking up of the suture-loaded holder in the distal portion may be repeated as needed to suture together tissue in the surgical cavity without having to withdraw the suture passer from the surgical cavity.

According to an aspect, a suture passer includes a first shaft comprising a hollow tube and a distal portion located distally of a distal end of the hollow tube; a needle comprising a needle tip and a needle shaft translatably mounted in the hollow tube and having a distal portion that is extendable out of the distal end of the hollow tube for passing a suture loaded holder through tissue positioned between the distal end of the hollow tube and the distal portion of the first shaft via a stroke of the needle; an actuatable engagement located in the distal portion of the first shaft for retaining the suture loaded holder in the distal portion of the first shaft after the suture loaded holder has passed through the tissue; a sheath extending around an exterior of the needle shaft and translatable with the needle shaft for at least a portion of a stroke of the needle shaft, wherein the sheath is moveable relative to the needle shaft for actuating the engagement to an unlatched position to release the holder from the distal portion of the first shaft.

Optionally, relative movement of the sheath to the needle shaft may include a rotational movement of the sheath about a longitudinal axis of the needle shaft.

Optionally, relative movement of the sheath to the needle shaft may include a translational movement of the sheath along a longitudinal axis of the needle shaft.

Optionally, relative movement of the sheath to the needle shaft may be controlled by a cam directly connected to the sheath or operatively connected to the sheath via a cam follower attached to the sheath.

Optionally, the actuatable engagement may be moved to a latched position by movement of the holder into the distal portion via the stroke of the needle.

Optionally, the suture passer may include an arm that comprises the actuatable engagement at the distal portion of the first shaft and an actuating surface positioned proximal to the actuatable engagement.

Optionally, the sheath may be configured to actuate the actuatable engagement by interfacing with the actuating surface, and when the sheath interfaces the actuating surface via relative movement to the needle shaft, the actuatable engagement is pushed away from the holder from the latched position to an unlatched position.

Optionally, as the sheath moves to actuate the actuatable engagement to the unlatched position, the holder may be released from the distal portion and securely mounted to the needle shaft via movement of the one or more tabs of the holder towards a recess of the needle shaft by the sheath.

Optionally, the actuating surface of the arm may be positioned in the distal portion of the first shaft.

Optionally, the actuating surface of the arm may be positioned proximally of the distal portion.

Optionally, the arm may include a living hinge.

Optionally, the holder may be a ferrule.

Optionally, the needle tip may be removably attached to the needle shaft and the needle tip is the holder.

Optionally, the suture passer may include the suture loaded holder.

Optionally, the holder may include an inner portion configured to interface with the needle shaft for mounting the holder onto the needle shaft via a friction fit or may include an inner portion having one or more movable tabs configured to move into a slot of the needle shaft, and when the actuatable engagement is in the latched position, the holder is secured in the distal portion of the first shaft so that the holder can be unmounted from the needle shaft.

Optionally, the suture passer may include a first trigger operatively connected to the sheath and needle shaft and when the holder is mounted on the needle shaft and the first trigger is pressed, the holder is moved with the needle via a stroke of the needle to the distal portion of the first shaft.

Optionally, the holder may include: one or more tabs configured to secure suture to the holder, an inner portion configured for receiving the needle shaft within the inner portion, and an exterior portion configured to interface with the sheath.

Optionally, the holder may include a tab configured to deflect inwards towards the needle shaft inserted within the holder for retaining the needle shaft within the holder.

Optionally, the tab may be movable by a translational movement of the sheath.

Optionally, the tab may be movable by a rotational movement of the sheath.

Optionally, the suture passer may include a first trigger operatively connected to the sheath and the needle shaft, wherein pressing the first trigger causes the sheath to translate together with the needle shaft to the distal portion of the first shaft, and wherein releasing the pressed first trigger causes the sheath to translate together with the needle shaft away from the distal portion of the first shaft.

Optionally, the first trigger may include a lock for latching the first trigger in a pressed position.

Optionally, the first trigger may be operatively connected to the sheath and the needle shaft via a rotatable cam.

Optionally, movement of the first trigger in a first direction may cause the sheath to translate together with the needle shaft to the distal portion, and after or as the sheath and the needle shaft translate to the distal portion, the sheath is configured to rotate in a rotational direction about the needle shaft and movement of the first trigger in a second direction causes the sheath to translate together with the needle shaft away from the distal portion and after or as the sheath and the needle shaft translate away from the distal portion, the sheath is configured to rotate about the needle shaft in the rotational direction.

Optionally, the suture passer may include a second trigger configured to move the sheath relative to the needle shaft to actuate the actuatable engagement to an unlatched position and press one or more tabs of the ferrule into a recess of the needle for securing the holder to the needle shaft, and movement of the second trigger causes the first trigger to move to a pressed position.

Optionally, the first trigger and the second trigger may be operatively connected to the sheath and the needle shaft via a cam comprising a first track for a first follower attached to the sheath and a second track for a second follower attached to the needle.

Optionally, movement of the first trigger may cause the first follower and the second follower to move simultaneously, and movement of the second trigger subsequent to movement of the first trigger may cause the first follower to move relative to the second follower.

Optionally, the distal portion of the first shaft may include one or more holes configured to allow tissue to pass through to prevent jamming of tissue at the distal portion.

Optionally, the distal portion of the first shaft may include a second portion connected to the first portion, the second portion having a tapered internal diameter.

According to an aspect, a method for passing a suture through tissue may include: positioning the tissue between a distal end of a hollow tube of a first shaft of a suture passer and a distal portion of the first shaft positioned distally of the distal end of the hollow tube; translating a distal portion of a needle through the tissue to the distal portion of the first shaft to retrieve a suture loaded holder retained in the distal portion, the needle comprising a needle tip and a needle shaft, the needle shaft is translatably mounted in the hollow tube; translating a sheath extending around an exterior of the needle shaft with the needle through the tissue to the distal portion of the shaft; actuating a moveable engagement to an unlatched position to release the suture loaded holder from the distal portion of the first shaft via movement of the sheath relative to the needle shaft.

Optionally, movement of the sheath relative to the needle shaft may include rotating the sheath about a longitudinal axis of the needle shaft.

Optionally, movement of the sheath relative to the needle shaft may include translating the sheath along a longitudinal axis of the needle shaft.

Optionally, movement of the sheath relative to the needle may be controlled by a cam directly connected to the sheath or operatively connected to the sheath via a cam follower attached to the sheath.

Optionally, the suture passer may include an arm that comprises the moveable engagement at the distal portion of the first shaft and an actuating surface positioned proximal to the moveable engagement, wherein the sheath engages the actuating surface to actuate the moveable engagement.

Optionally, actuating the moveable engagement to release the holder from the distal portion of the first shaft may include interfacing the sheath with the actuating surface via relative movement to the needle shaft, and pushing away the moveable engagement from the holder from a latched position to the unlatched position.

Optionally, as the sheath moves to actuate the actuatable engagement to the unlatched position, the holder may be released from the distal portion and securely mounted to the needle shaft via movement of one or more tabs of the holder towards a recess of the needle shaft by the sheath.

Optionally, the actuating surface of the arm may be positioned in the distal portion of the first shaft.

Optionally, the actuating surface of the arm may be positioned proximally of the distal portion.

Optionally, the arm may include a living hinge.

Optionally, the method may include interfacing an inner portion of the holder with the needle shaft for mounting the holder onto the needle shaft via a friction fit or interfacing an inner portion of the needle shaft having one or more movable tabs configured to move into a slot of the needle shaft for mounting the holder onto the needle shaft, and securing the holder in the distal position of the first shaft so that the holder can be unmounted from the needle shaft when the moveable engagement is in a latched positioned.

Optionally, the method may include pressing a first trigger when the holder is mounted on the needle shaft to move the holder with the needle via translation of the needle to the distal portion of the first shaft, the first trigger being operatively connected to the sheath and needle.

Optionally, the holder may include: one or more first tabs configured to secure suture to the holder, an inner portion configured for receiving the needle shaft within the inner portion, and an exterior portion configured to interface with the sheath.

Optionally, the method may include deflecting a second tab of the holder inwards towards the needle shaft inserted within the holder for securing the holder to the needle shaft.

Optionally, deflecting the second tab may include translational movement of the sheath.

Optionally, deflecting the second tab may include rotational movement of the sheath.

Optionally, the method may include pressing a first trigger operatively connected to the sheath and the needle to translate the sheath with the needle through the tissue to the distal portion of the first shaft, and the method comprises releasing the pressed first trigger to translate the sheath together with the needle away from the distal portion of the first shaft.

Optionally, the method may include latching the first trigger in a pressed position via a lock.

Optionally, the first trigger may be operatively connected to the sheath and the needle shaft via a rotatable cam.

Optionally, the method may include moving the first trigger in a first direction to translate the sheath together with the needle shaft to the distal portion, moving the first trigger in a second direction to translate the sheath together with the needle shaft away from the distal portion of the first shaft, and rotating the sheath in a rotational direction about the needle shaft after or as the sheath and the needle shaft translate to and from the distal portion.

Optionally, the method may include moving a second trigger to a pressed positioned to actuate the moveable engagement to rotate the sheath in the rotational direction about the needle shaft.

Optionally, the first trigger and the second trigger may be operatively connected to the sheath and the needle via a cam comprising a first track for a first follower attached to the sheath and a second track for a second follower attached to the needle.

Optionally, moving the first trigger may cause the first follower and the second follower to move simultaneously, and moving the second trigger subsequent to moving of the first trigger causes the first follower to move relative to the second follower.

Optionally, the method may include: repositioning the tissue between the distal end of the hollow tube of the first shaft of the suture passer and the distal portion of the first shaft positioned distally of the distal end of the hollow tube; translating the distal portion of the needle shaft mounted in the hollow tube and the suture loaded holder mounted on the needle through the tissue to the distal portion of the first shaft; translating once again the sheath with the needle shaft through the tissue to the distal portion of the first shaft; and actuating the moveable engagement positioned in the distal portion of the first shaft for retaining the suture loaded holder in a latched position in the distal portion of the first shaft.

Optionally, the method may include allowing tissue to pass through one or more holes of the distal portion of the first shaft to prevent jamming of tissue at the distal portion.

Optionally, the distal portion of the first shaft may include a second portion connected to the first portion, the second portion having a tapered internal diameter.

BRIEF DESCRIPTION OF THE FIGURES

The disclosure will now be described, by way of example only, with reference to the accompanying drawings, in which:

FIGS. 6A-6C show exemplary schematics that illustrate a progression for retrieving a ferrule from the distal portion of a suture passer;

FIG. 9A shows a cross-sectional view of an exemplary ferrule;

FIGS. 9B-9D show an exemplary progression for mounting a ferrule to a needle;

FIG. 11 shows a schematic illustrating exemplary positioning of a sheath and a needle in a tissue engaging region of a suture passer;

DETAILED DESCRIPTION

Figure 1:
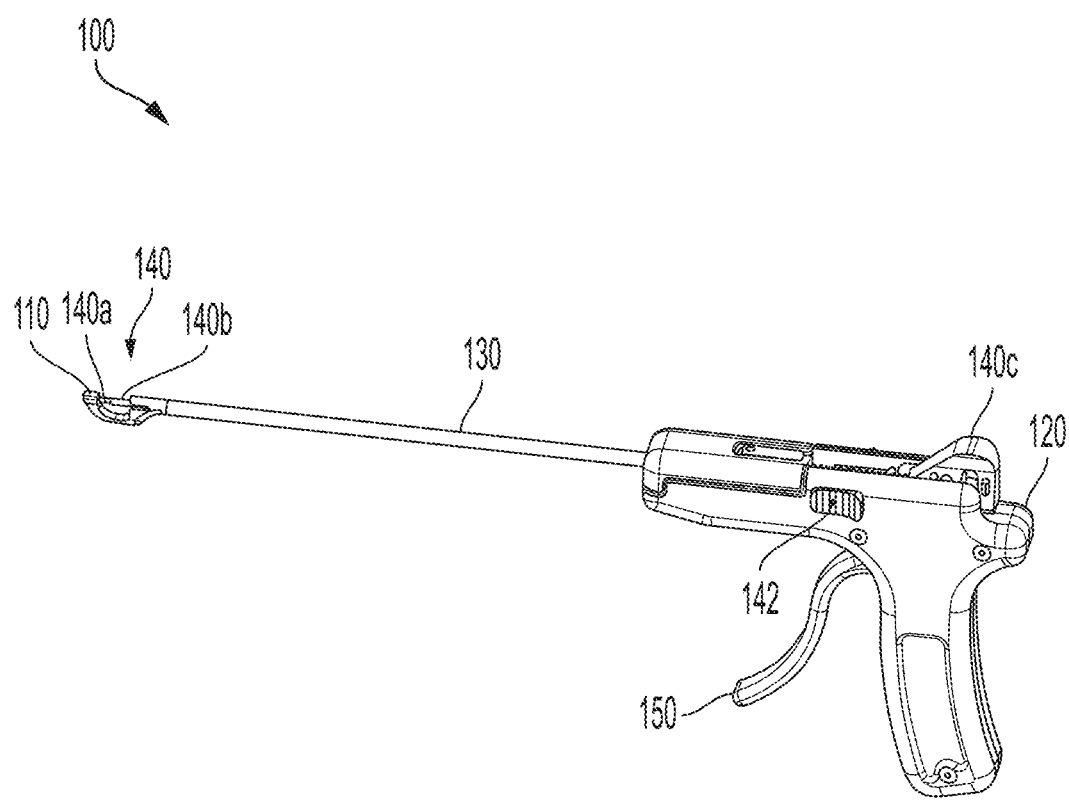
FIG. 1 shows an exemplary suture passer.

Reference will now be made in detail to implementations and examples of various aspects and variations of devices, systems, and methods described herein. Although several exemplary variations of the devices, systems, and methods are described herein, other variations of the devices, systems, and methods may include aspects of the devices, systems, and methods described herein combined in any suitable manner having combinations of all or some of the aspects described.

Disclosed herein are examples of devices, systems, and methods for repeatedly passing suture through tissue without requiring removal of the suture passer from the surgical cavity. An exemplary suture passer passes a suture-loaded suture holder back and forth through the tissue. The suture holder with its loaded suture is mounted on a needle of the suture passer and passed distally through the tissue via a distal movement of the needle. After passing through the tissue, the suture-loaded holder is moved into a distal portion of the suture passer through continued distal movement of the needle. The distal portion retains the suture-loaded holder as the needle retracts back through the tissue. After the needle retracts, the suture passer can be repositioned on the tissue and the needle can then be passed through a different portion of the tissue. The needle picks up the suture holder from the distal portion of the suture passer and pulls it back through the tissue. In this way, suture can be repeatedly passed back and forth through tissue without needing to withdraw the suture passer from the surgical cavity.

The suture holder may be retained in the distal portion of the suture passer on a first needle stroke and may be released from the distal portion of the suture passer on a second needle stroke. For example, on the first needle stroke towards the distal portion of the suture passer, the suture holder mounted to the needle is passed through tissue to the distal portion of the suture passer via distal movement of the needle and retained in the distal portion of the suture passer by a moveable component that engages the suture holder. The moveable component may engage the suture holder by snapping into a recess of the suture holder due to a bias of the moveable component. Engagement of the moveable component in the recess of the suture holder overcomes any frictional force between the suture holder and the needle (or any other retention feature) that would otherwise tend to retain the suture holder on the needle as the needle retracts back through tissue. Thus, engagement of the suture holder by the moveable component causes the suture holder to dismount from the needle as it remains retained in the distal portion of the suture passer upon retraction of the needle back through tissue.

On the second stroke of the needle to the distal portion of the suture passer, the moveable component may be moved out of engagement with the suture holder. For moving the moveable component out of engagement with the suture holder, the suture passer can include a sheath that passes through the tissue along with the needle. The sheath may be configured to extend concentrically about an exterior surface of the needle. When the needle and sheath reach the distal portion, the sheath causes the moveable component to move out of engagement with the suture holder and the needle re-engages the suture holder. Since the moveable component is not engaged with the suture holder, the suture holder can release from the distal portion and retract back through the tissue away from the distal portion of the suture passer via proximal movement of the needle.

The first trigger may actuate the first stroke of the needle and the second stroke of the needle. For example, for actuating the first stroke of the needle, a user may press the first trigger in a first direction which causes the needle, the suture holder mounted to the needle, and the sheath extending about the needle to move distally through tissue to the distal portion of the suture passer. Upon release of the first trigger subsequent the first stroke of the needle, the needle and the sheath can retract proximally through tissue away from the distal portion of the suture passer as the suture holder remains in the distal portion. After the needle and the sheath have retracted away from the distal portion, the user may press the first trigger again to actuate the second stroke of the needle which causes the needle and the sheath extending about the needle to move distally through tissue to the distal portion of the suture passer. In response to the second stroke actuated by user actuation of the first trigger, the sheath may move relative to the needle via a cam operationally connected to the first trigger and the sheath. As the sheath moves relative to the needle, the sheath releases the suture holder from the distal portion and the needle re-engages the suture holder. Upon release of the first trigger subsequent the second stroke, the needle, the suture holder remounted to the needle, and the sheath retract proximally through tissue away from the distal portion of the suture passer.

Optionally, a movable cam of the suture passer may control movement of the sheath relative to the needle. The movable cam may be operably connected to the first trigger and the sheath and may include a recessed track that is configured to engage a stationary pin of the suture passer. Engagement of the recessed track of the cam and the stationary pin of the suture passer may limit movement of the cam to a path of the recessed track. Thus, as the movable cam moves due to actuation of the first trigger, the movement of the cam follows a path of the recessed track due to the stationary pin engaged with the recessed track. The recessed track may include straight portions and curved portions. The recessed track may include a step to limit rotational movement of the cam to a first rotational direction. For every actuation and release of the first trigger, the cam operably connected to the first trigger may move a pre-determined amount of degrees in the first rotational direction, a pre-determined translational distance, or a combination thereof.

A position of the sheath based on a position of the movable cam may differentiate the second stroke of the needle from the first stroke of the needle. For example, the cam may move to a passing position as the needle completes the first stroke of the needle and may move to a retrieving position as the needle completes the second stroke of the needle. During the first stroke of the needle, the sheath moves along with the needle distally to the distal portion of the suture passer based on movement of the cam to the passing position. As the cam moves to the passing position, the sheath moves relative to the needle to a position in which a slot of the sheath accommodates an actuating surface operably coupled to the moveable component so that the movable component is not actuated by the sheath. With the slot of the sheath accommodating the actuating surface operably coupled to the moveable component, the suture-loaded holder is retained in the distal portion as described above and further below. During the second stroke of the needle, the sheath moves along with the needle distally to the distal portion of the suture passer based on movement of the cam to the retrieving position. As the cam moves to the retrieving position, the sheath moves relative to the needle to a position in which the sheath actuates the actuating surface coupled to the moveable component. In this position, the slot of the sheath is no longer positioned to accommodate the actuating surface coupled to the movable component. The actuation of the actuating surface coupled to the movable component by the sheath releases the suture-loaded holder from the distal portion of the suture passer as described above and further below. Movement of the cam from the passing position to the retrieving position and from the retrieving position to the passing position may include a rotational movement, a translational movement, or a combination thereof. Movement of the cam from the passing position to the retrieving position follows a first path of the recessed track and movement of the cam from the retrieving position to the passing position follows a second path of the recessed track. The first path and the second path may form a continuous path of the recessed track.

Movement of the sheath relative to the needle may cause the sheath to move the moveable component engaged with the suture holder in the distal portion out of engagement with the suture holder. Movement of the sheath relative to the needle may include rotation of the sheath, further distal translation of the sheath, or a combination thereof. The movement of the sheath relative to the needle may move an actuating surface of the sheath to a position in which the actuating surface of the sheath pushes against an actuating surface of an arm operably coupled to the moveable component causing the arm to move. Movement of the arm causes the moveable component of the distal portion of the suture passer to disengage from the suture-loaded holder and thus release the suture-loaded holder from retention in the distal portion of the suture passer. Optionally, the arm of the suture passer may include the moveable component.

The actuating surface of the arm may be located in the distal portion of the suture passer or in a portion of the suture passer that is proximal to the tissue engaging recess of the suture passer. In accordance with the actuating surface of the arm being located in the portion proximal to the tissue engaging recess, the actuating surface of the sheath may be located in the portion proximal to the tissue engaging recess such that the actuating surface of the sheath and the actuating surface of the arm may contact each other as a result of movement of the sheath relative to the needle. In accordance with the actuating surface of the arm being located in the distal position of the suture passer, the actuating surface of the sheath may be located in the distal portion of the suture passer such that the actuating surface of the sheath and the actuating surface of the arm may contact each other as a result of movement of the sheath relative to the needle. The arm may include a living hinge so that movement of the actuating surface (either in the distal portion or proximal portion of the suture passer) of the arm causes movement of the actuatable engagement in the distal portion of the suture passer.

Movement of the sheath relative to the needle may cause the sheath to move to a holding position in which the sheath holds the suture holder fixed against the needle. The sheath may hold the suture against the needle by pushing and holding one or more first tabs of the suture holder towards a recess of the needle. With the sheath holding the suture holder against the needle, the suture holder may be retracted through tissue away from the distal portion of the suture passer with proximal movement of the needle. Movement of the sheath to the holding position may include further distal translation of the sheath in the distal portion relative to the needle. Movement of the sheath to the holding position may include rotation of the sheath relative the needle.

The suture passer may include a movable cam configured to control movement of the sheath relative to the needle. The cam may be operationally connected to the first trigger so that release of the first trigger causes the sheath to move relative to the needle via the cam control. The cam may be rotational, translational, or both rotational and translational.

The suture passer may include a plurality of user actuatable triggers. The triggers may be actuated, for example, by a user pressing one or more triggers. User actuation of a first trigger of the plurality of triggers may cause the needle and the sheath to move distally to the distal portion of the suture passer and subsequent release of the user actuation of the first trigger may cause the needle and the sheath to retract proximally away from the distal portion of the suture passer. Similar to the above description regarding examples having a single trigger, a first user actuation of the first trigger may actuate a first stroke of the needle to the distal portion. During the first stroke, the suture holder may be mounted to the needle and move with the needle to the distal portion. As described above in reference to the single trigger, after the first stroke, the suture holder may be retained in the distal portion as the needle and the sheath retract proximally away from the distal portion. A second user actuation of the first trigger may actuate a second stroke of the needle and the sheath to the distal portion. Subsequent the second user actuation of the first trigger, the needle and the sheath are in the distal portion of the suture passer. While the first trigger remains actuated by the second user actuation, user actuation of a second trigger of the plurality of triggers causes the sheath to move relative to the needle in the distal portion of the suture passer. As described above and further below, movement of the sheath relative to the needle can move a movable component engaged with the suture holder in the distal portion out of engagement with the suture holder. Actuation of the second trigger may mechanically override one or more tracks of a cam configured to control movement of the sheath relative to the needle.

Optionally, the sheath may be operatively connected to the first trigger and to the second trigger via cam control. Subsequent actuation of the first trigger, the sheath may move via cam control in a distal direction to the distal portion and stop at a first distal position. When the second trigger is actuated after the first trigger is actuated, the sheath may move via the cam control relative to the needle to a second distal position located distal to the first distal position for retrieving the suture holder.

The suture passer may include a trigger lock for holding the first trigger in a pressed position. In the pressed position, the needle may be positioned in the distal portion of the suture passer. The first trigger may remain in the pressed position unless the second trigger is actuated or the trigger lock is moved to an unlocked position.

The suture-loaded holder may be mounted to the needle via a friction fit. That is, the suture holder may include one or more second tabs configured to contact the needle when the needle is positioned in the suture holder. The one or more second tabs of the suture holder in contact with the needle may be configured to hold the suture holder on the needle via friction. The friction force is not changed by sheath position.

Optionally, as the suture holder mounted to the needle is moved by movement of the needle to and from the distal portion of the suture passer, the sheath can be configured to cover at least a portion of the suture holder. That is, while the suture holder is mounted to the needle, the sheath can be configured to cover the portion of the suture holder. Accordingly, when the suture holder is released from the distal portion of the suture passer and remounted on the needle, the sheath covers the portion of the suture holder. The portion of the suture holder may be covered by the sheath during translation movement of the needle to and from the distal portion until the sheath moves relative to the needle. As the suture holder is unmounted from the needle and retained in the distal portion of the suture passer, the sheath is configured to uncover the portion of the suture holder. The portion of the suture holder may be a proximal portion of the suture holder.

The needle may include a needle tip and a needle shaft. The suture holder may be mounted and unmounted about an external surface of the needle shaft via movement of the moveable component as described above and further below. The needle tip and the needle shaft may be configured to pass through an interior of the suture holder during mounting and unmounting of the suture holder to the needle shaft. The needle tip may be fixed to the needle shaft.

The needle shaft may be hollow for receiving the suture-loaded holder. The hollow needle shaft may include an inwardly extending portion for engaging a corresponding recessed portion of the suture holder. When the suture holder is positioned in the hollow needle shaft, the suture-loaded holder may be mounted to the hollow needle shaft by engaging the inwardly extending portion of the needle shaft with the recessed portion of the suture-loaded holder. The recessed portion of the suture-loaded holder may be recessed from an external surface of the suture-loaded holder and the inwardly extending portion of the needle shaft may extend from an internal surface of the needle shaft.

Figure 12A:
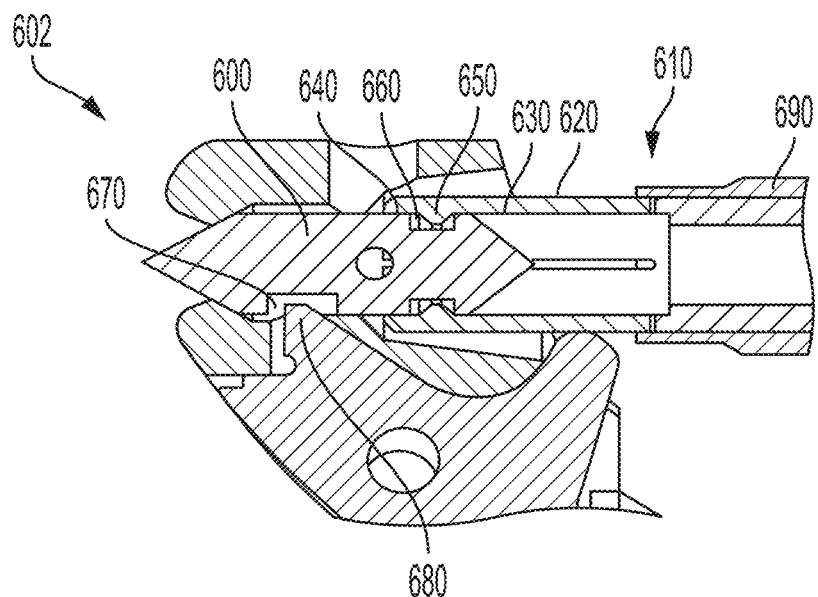
FIG. 12A shows a cross-sectional view of an exemplary suture holder removably attached to a needle shaft.
Figure 12B:
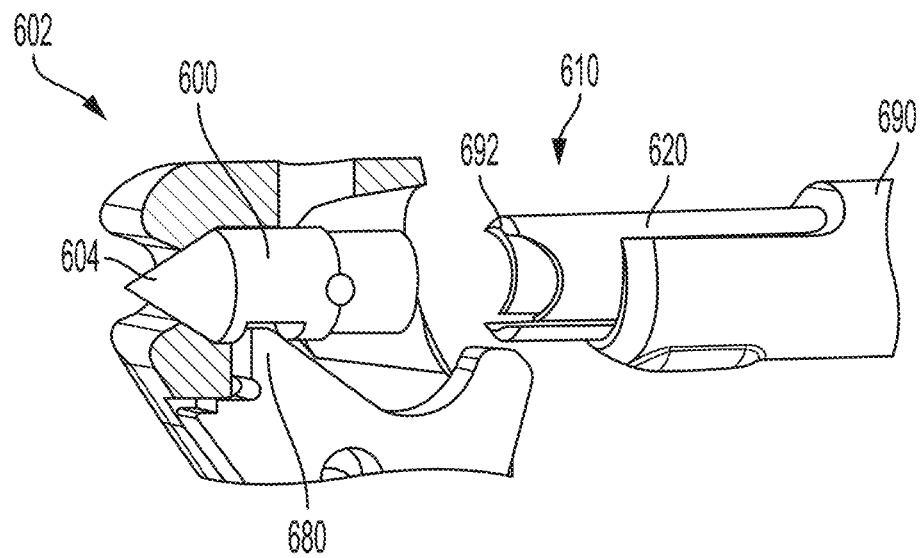
FIG. 12B shows an exemplary suture holder in a detached configured, wherein the suture holder is detached from a needle shaft.

Optionally, the suture holder may be a ferrule. The ferrule may have an annular shape and the ferrule may be configured to mount the needle shaft. FIGS. 1-10 show examples in which the suture holder is a ferrule and the needle comprises a needle tip fixed to the needle shaft. Optionally, the suture holder forms the needle tip. FIGS. 12A-12B show an example in which the suture holder forms the needle tip and the needle tip may be attached and detached to the needle shaft.

In addition, it is also to be understood that the singular forms "a", "an," and "the" used in the following description are intended to include the plural forms as well, unless the context clearly indicates otherwise. It is also to be understood that the term "and/or," as used herein, refers to and encompasses any and all possible combinations of one or more of the associated listed items. It is further to be understood that the terms "includes," "including," "comprises," and/or "comprising," when used herein, specify the presence of stated features, integers, steps, operations, elements, components, and/or units, but do not preclude the presence or addition of one or more other features, integers, steps, operations, elements, components, units, and/or groups thereof.

In the following description of the disclosure and examples, reference is made to the accompanying drawings in which are shown, by way of illustration, specific examples that can be practiced. It is to be understood that other examples and examples can be practiced, and changes can be made, without departing from the scope of the disclosure.

FIG. 1 shows an exemplary suture passer 100. The suture passer 100 may be configured for continuously suturing tissue while the suture passer 100 remains in the surgical cavity. The suture passer 100 may include a handle portion 120 and a shaft 130 that extends from the handle portion 120. The shaft 130 may include a tissue engaging recess 110 and may be configured to at least partially house a translatable needle 140 of the suture passer 100. Tissue may be positioned in the tissue engaging recess 110 of the suture passer so that the tissue is in a position to receive suture from the suture passer 100. The handle portion 120 may include a trigger 150 configured to move the translatable needle 140 within the shaft 130 and through tissue positioned in the tissue engaging recess 110.

Suture passer 100 can be used for suturing tissue in a surgical cavity during minimally invasive surgeries. The surgical cavity may be in a joint which, due to the anatomy of the joint, is considered a "tight" joint in that the joint is anatomically more constricted than "spacious" joints like a shoulder or knee joint. During minimally invasive surgery, the tissue engaging recess 110 of the suture passer 100 loaded with suture may be inserted into the surgical cavity, either with or without a cannula, to position the suture passer 100 for suturing tissue. Tissue may be positioned in the tissue engaging recess 110 inserted into the surgical cavity.

A surgeon may use the suture passer 100 to repeatedly pass suture through tissue positioned in the tissue engaging recess 110 without removing the suture passer 100 from the surgical cavity between suture passes. To pass suture through different portions of tissue, the surgeon may reposition tissue in the engaging portion 110 or reposition the suture passer 100 to reposition the tissue engaging recess 110 around a portion of tissue. The surgeon does not have to remove the suture passer 100 from the surgical cavity after each pass through tissue to reload the suture passer 100 with suture. In this way, suturing tissue in anatomically constricted spaces, just as a hip joint, can be performed without moving the suture passer 100 in and out of the surgical cavity, and thus facilitates more efficient and feasible suturing in "tight" joints.

The suture passer 100 may be used to suture physically tough tissue that is located in anatomically constrained spaces of the body. For example, the suture passer 100 may be used to suture fibrous capsule of a hip joint. The fibrous capsule is typically difficult for a surgeon to suture together by hand due to the toughness of the tissue and the location of the tough tissue in the hip joint. A needle having an appropriate piercing diameter for piercing through tough tissue may be loaded into the suture passer 100. The needle 140 may include a needle tip 140a, a needle shaft 140b, and a needle handle 140c. The needle 140 may pre-assembled as part of the suture passer 100.

The needle 140 may be replaceable and disposable and the suture passer 100 may be reusable. A surgeon may load the disposable needle 140 into the suture passer 140 by inserting the needle tip 140a into the shaft 130 of the suture passer and guiding the needle tip 140a to the tissue engaging recess 110 of the shaft 130. The needle handle 140c may be translatably locked in the handle portion 120 of the suture passer 100 via a needle latch 142.

Figure 2A:
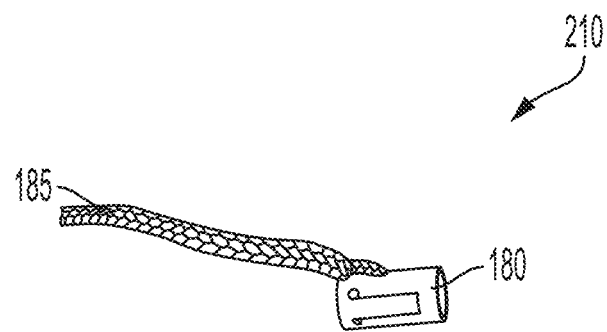
FIGS. 2A-2C show exemplary ferrules for loading with suture.

A suture holder, which can be, for example, in the form of a ferrule 180, may be loaded with implantable suture. FIG. 2A shows an example of the ferrule 180 loaded with implantable suture 185 to form an assembly of a suture-loaded ferrule 210. The ferrule 180 may be loaded with suture may be mountable to the needle 140 and retained in the distal portion 170. The ferrule 180 and the implantable suture 185 may be replaceable and disposable. A user of the suture passer 100 may load the implantable suture 185 to the ferrule 180. The ferrule 180 may be pre-loaded with implantable suture 185. The ferrule 180 pre-loaded with suture and the suture passer 100 may be packaged as a suture kit.

Figure 2B:
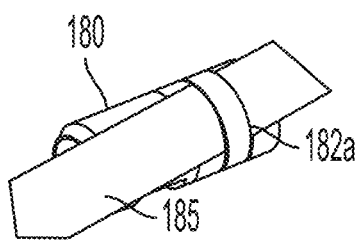
Figure 2C:
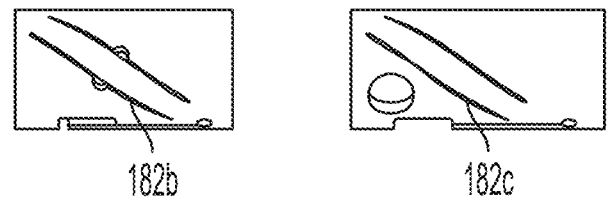

FIG. 2B shows an exemplary schematic of implantable suture 185 secured onto the ferrule 180 through at least one slot 182a. FIG. 2C shows an exemplary schematic of two ferrule profiles that have one or more slots 182b, 182c for securing implantable suture 185. The implantable suture 185 may be wound via a torturous path through ferrule 180, and crimped or welded to the one or more slots to securely attach the implantable suture 185 to the ferrule 180.

Figure 3A:
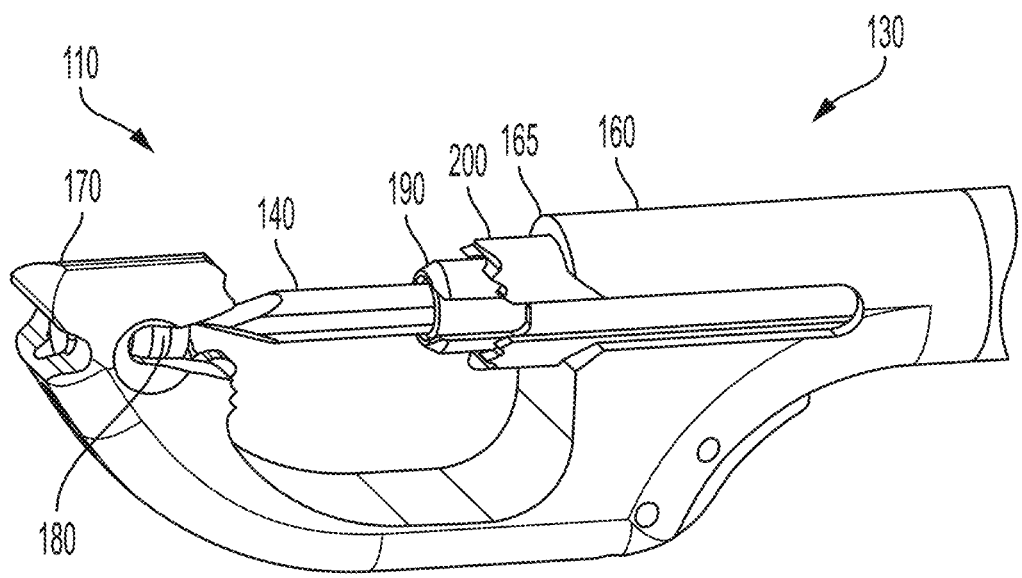
FIG. 3A shows an exemplary tissue engaging recess of a suture passer.

FIG. 3A shows an exemplary tissue engaging recess 110 of the shaft 130. The tissue engaging recess 110 may include a hollow tube 160 of the shaft 130 and a distal portion 170 of the shaft 130 positioned distally from a distal end 165 of the hollow tube 160. The needle 140 may be translatably mounted in the hollow tube 160 and may be extendable out of the distal end 165 of the hollow tube 160 and moveable to the distal portion 170 via a stroke of the needle. A stroke of the needle 140 may include a translational movement of the needle 140 from the distal end 165 of the hollow tube 160 into the distal portion 170. The stroke of the needle may a result, for example, from user actuation of a trigger (such as trigger 150).

The suture passer 100 may include a sheath 190. The sheath 190 may extend around an exterior of the needle 140 and may be translatable with the needle 140 for at least a portion of the needle movement towards and away from the distal portion 170. The sheath 190 may be configured to rotate or translate relative to the needle 140 based on pressing or releasing a trigger (such as trigger 150). The relative movement of the sheath 190 to the needle 140 may include a rotational movement of the sheath 190 about a longitudinal axis of the needle 140. The relative movement of the sheath to the needle may include a translational movement of the sheath along a longitudinal axis of the needle.

The suture passer 100 may include a moving jaw 200 configured to extend around the sheath 190 and move between the distal portion 170 and the distal end 165 of the hollow tube 160. The moving jaw 200 may move with the needle 140 for gripping tissue positioned in the tissue engaging region 110. Alternatively, the moving jaw 200 may move relative to the needle 140 upon user actuation of a trigger (such as trigger 150).

As shown in the example of FIG. 3A, a suture holder in the form of a ferrule 180 may be configured to be retained in the distal portion 170. The suture passer 100 may include the ferrule 180. The ferrule 180 may be configured to mount to a shaft portion of the translatable needle 140. The ferrule 180 may be configured to receive the needle 140 within an interior portion of the ferrule 180 and mount to the needle 140 inserted within the ferrule 180. The mounted ferrule 180 may move with the needle 140 for at least a portion of the needle movement between the distal portion 170 and the distal end 165 of the hollow tube 160.

Figure 3B:
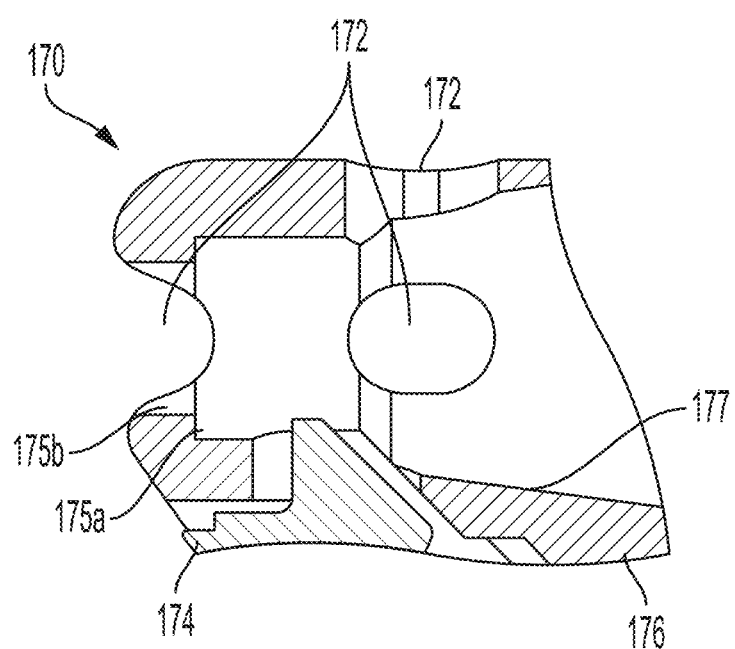
FIG. 3B shows an exemplary distal portion of a tissue engaging recess.

FIG. 3B shows an example of the distal portion 170 configured to receive and retain the ferrule 180. In the example of FIG. 3B, the distal portion 170 includes one or more apertures or openings 172 for preventing tissue from jamming the distal portion 170. That is, as tissue is pushed towards the distal portion 170 on strokes of the needle 140, the tissue may exit the distal portion 170 through the one or more apertures 172. In this way, the one or more apertures 172 help prevent tissue jamming at the distal portion 170 which would make movement of the ferrule 180 in and out of the distal portion 170 difficult.

The distal portion 170 may include a distal end 174 and a proximal end 176. The distal end 174 may include a stopping surface 175a configured to prevent an inserted ferrule from moving further distally into the distal end 174. The distal end 174 may include an inner surface 175b configured to interface with an outer surface of the needle 140 so that tissue is prevented from entering the distal end 174 and interfering with a mechanism for retaining and releasing the ferrule in the distal portion 170. The stopping surface 175a may be located proximal to the inner surface 175b. The proximal end 176 of the distal portion 170 may include a tapered inner perimeter 177 to help prevent tissue from jamming at the proximal end 176 of the distal portion 170.

FIGS. 4A-4D show positions of the ferrule 180 in the distal portion 170 of the suture passer 100. As shown in FIGS. 4A-4D, the ferrule 180 initially mounted to the needle 140 is translated by the needle 140 to the distal portion 170 and retained in the distal portion 170 and unmounted from the needle by the distal portion 170. The ferrule 180 may be retained in the distal portion 170 by an actuatable engagement 220 located in the distal portion 170 of the suture passer. The actuatable engagement 220 is movable to a latched position due to a bias of the actuatable engagement 220.

Figure 4A:
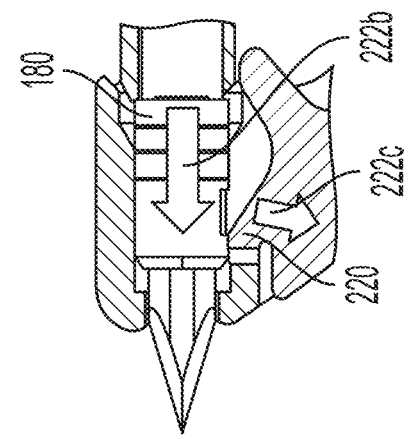
FIGS. 4A-4D show an exemplary progression for retaining a ferrule in a distal portion of a suture passer.

FIG. 4A shows the ferrule 180 in a first position in the distal portion 170 and mounted to the needle 140. In the example of FIG. 4A, the ferrule 180 was moved to the distal portion 170 via translational movement of the needle 140. As the ferrule 180 is moved in a first direction (as indicated by arrow 222a in FIG. 4A) in the distal portion 170, the ferrule 180 may contact the actuatable engagement 220 of the suture passer 100 and push it out of the way. The actuatable engagement 220 may be biased in an upward direction with respect to the orientation of the device shown in FIG. 4A. The actuatable engagement 220 may be part of an arm of the suture passer 100.

Figure 4B:
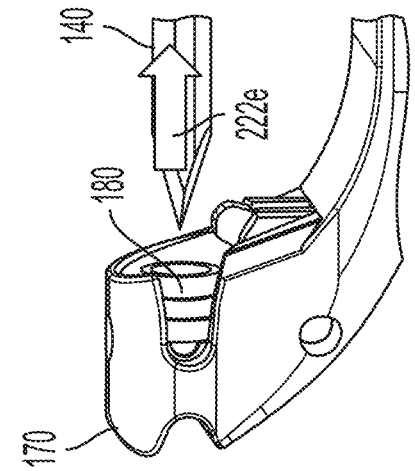

The ferrule 180 may be moved further distally from the first position to a second position in the distal portion 170 via distal movement of the needle 140 (as indicated by arrow 222b in FIG. 4B). In the example of FIG. 4B, the ferrule 180 is shown in the second position. The second position is distal to the first position shown in FIG. 4A. In the second position, the ferrule 180 pushes the actuatable engagement 220 against the bias in a second direction (as indicated by arrow 222c in FIG. 4B). As the ferrule 180 is moved further distally from the second position via distal movement of the needle 140, the ferrule 180 pushes and slides along the actuatable engagement 220.

Figure 4C:
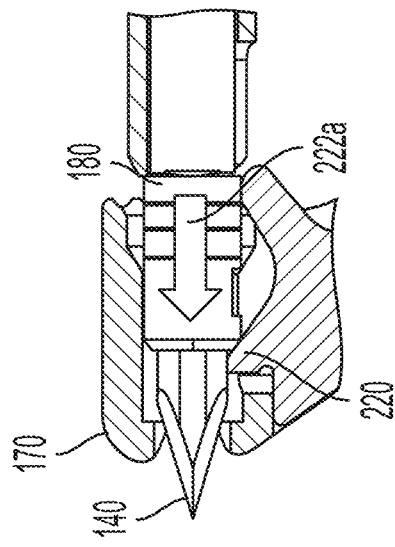

FIG. 4C shows a third position of the ferrule 180. The third position is distal to the second position and the ferrule 180 moves from the second position to the third position via distal movement of the needle 140. The third position may be a distal-most position of the ferrule 180 in the distal portion 170. When the ferrule 180 is the third position, the actuatable engagement 220 moves to a latched position by snapping into a recess 184 of the ferrule 180 due to the bias of the actuatable engagement 220. That is, the actuatable engagement is biased in a third direction (as indicated by arrow 222d in FIG. 4C) to snap into the recess 184 of the ferrule 180 when the ferrule 180 is in the third position. In the latched positioned, the ferrule is retained in the distal portion 170 of the suture passer 100 by the actuatable engagement 220 in the latched position. The actuatable engagement 220 biased towards the latched position prevents the ferrule 180 from moving out of the third position via proximal movement of the needle 140. That is, as the needle 140 moves proximally, the actuatable engagement 220 biased into the recess 184 of the ferrule 180 holds the ferrule 180 in place and overcomes any frictional force between the ferrule 180 and the needle 140 that would otherwise tend to retain the ferrule 180 on the needle 140. As this frictional force is overcome by the actuatable engagement 220 in the latched position, the ferrule 180 is unmounted from the needle 140 and retained in the distal portion 170.

The sheath 190 may move along with the needle 140 distally to the distal portion of 170 as the needle 140 passes the ferrule 180 to the third position. The sheath 190 may include a slot 192 that accommodates an actuating surface 230 of an arm 240 of the suture passer 100 so that the sheath 190 does not actuate the actuating surface 230 when the needle 140 passes the ferrule 180 to the third position. The arm 240 may include the actuating surface 230 and the actuatable engagement 220.

Figure 4D:
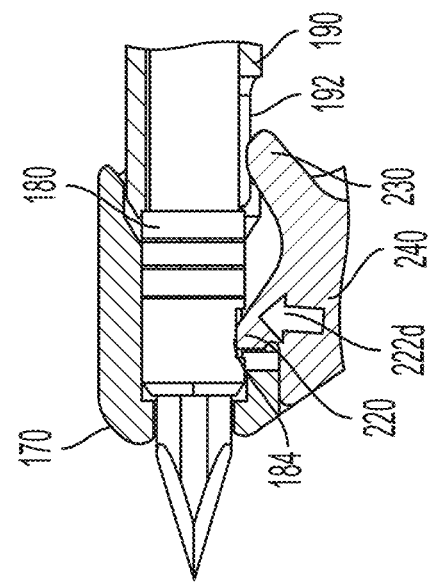

FIG. 4D shows the ferrule 180 retained in the third position in the distal portion 170 and unmounted from the needle 140. Since the ferrule 180 is retained in the third position and unmounted from the needle 140, retraction of the needle 140 away from the distal portion 170 (in a fourth direction as indicated by arrow 222e in FIG. 4) through tissue positioned in the tissue engaging region of the suture passer 100, leaves behind the ferrule 180 unmounted from the needle 140 in the third position in the distal portion 170. The needle 140 may be retracted through tissue in the proximal direction based upon user actuation of a trigger (such as trigger 150). The ferrule 180 may be unmounted from the needle 140 when the ferrule 180 is retained in the distal portion 170 and the needle 140 is retracted away from the distal portion 170 in the proximal direction.

After the ferrule 180 has been retained in the distal portion 170 and unmounted from the needle 140, the needle 140 is retracted away from distal portion back through tissue positioned in the tissue engaging region. When the needle 140 is retracted towards the hollow tube 160, a user of the suture passer 100 may reposition the tissue engaging region of the suture passer 100. In this way, user actuation of a trigger (such as trigger 150) may cause the needle 140 to move distally to the distal portion 170 through another portion of tissue to retrieve the ferrule 180 from the distal portion 170. The needle 140 may be re-inserted into the ferrule 180 by moving the needle 140 to distally to a distal-most position of the needle 140 in the distal portion 170 via actuation of a trigger (such as trigger 150). When the needle 140 is inserted in the ferrule 180, the ferrule 180 may be securely mounted to the needle 140 via a friction fit between the ferrule 180 and the needle 140. When the needle 140 is inserted in the ferrule 180, the ferrule 180 may be securely mounted to the needle 140 via one or more tabs of the ferrule 180 that are configured to snap into a recess of the needle 140, as discussed further below in reference to FIGS. 9A-9D.

Figure 5:
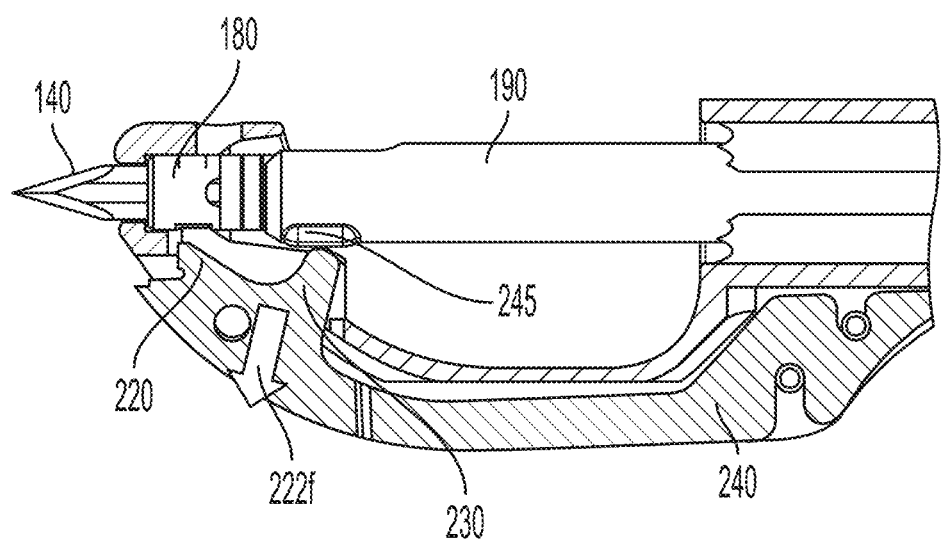
FIG. 5 shows an exemplary suture passer comprising an actuating surface.
Figure 8:
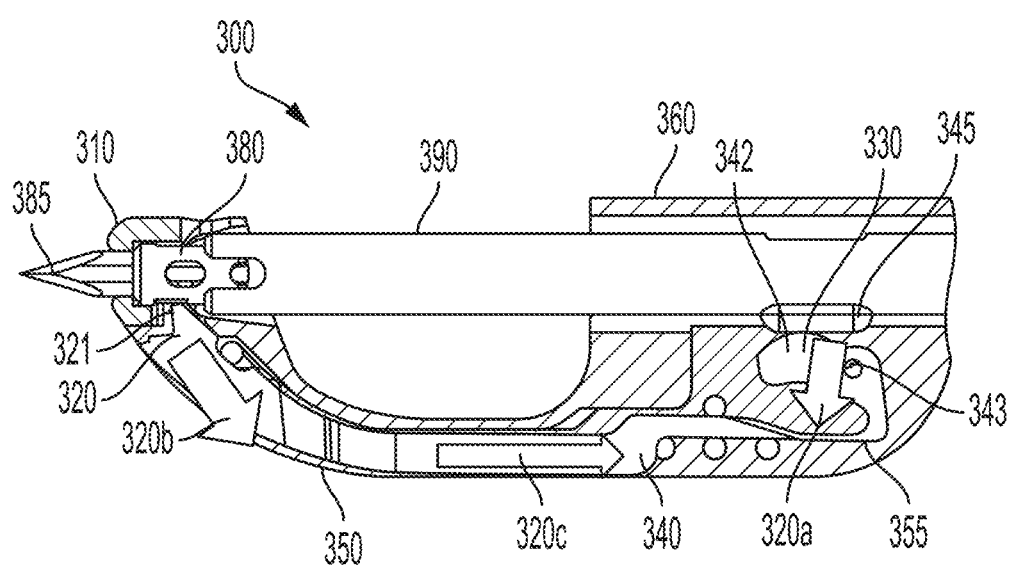
FIG. 8 shows an exemplary suture passer that includes an arm having an actuatable engagement and an actuating surface.

The ferrule 180 may be released from the third position in the distal portion 170 via actuation of the actuating surface 230 of the arm 240 of the suture passer 100 by the sheath 190. FIG. 5 shows an example of a position of the sheath 190 extending about the needle 140 in which the ferrule 180 may be released from the third position of FIGS. 4C-4D. Relative to FIG. 4C, the sheath 190 of FIG. 5 has rotated to a position in which the slot 192 no longer accommodates the actuating surface 230 of the arm 240. With the slot 192 no longer accommodating the actuating surface 230, an actuating surface 245 of the sheath 190 is positioned to actuate the actuating surface 230 of the arm 240. The actuating surface 230 of the arm 240 may be located in the distal portion 170 (as shown in FIG. 5) or in hollow tube 160 (as shown in FIG. 8) of the suture passer 100. In the example of FIG. 5, the actuating surface 230 of the arm 240 is located in the distal portion 170 proximal to the actuatable engagement 220 of the arm 240. Movement of the sheath 190 relative to the needle 140 may move the actuating surface 245 of the sheath to a position in which the actuating surface 245 pushes the actuating surface 230 of the arm against the bias of the actuatable engagement 220 in a direction indicated by arrow 222f in FIG. 5. When the actuating surface 230 of the arm is pushed by the actuating surface 245 of the sheath 190, the actuatable engagement 220 is pushed out of the latched position to an unlatched position, and thus no longer retains the ferrule 180 in the third position in the distal portion 170. The movement of the sheath 190 relative to the needle 140 may include be a rotational movement or a translational movement. The ferrule 180 may be mounted to the needle 140 as the actuatable engagement 220 moves to the unlatched position.

The motion of the sheath relative to the needle may be controlled by a cam attached to the sheath. Motion of the cam may be controlled by the trigger in the handle portion of the suture passer. FIGS. 6A-6C show an example of passing the ferrule 180 to the distal portion 170 of the suture passer via a trigger 150 and a cam 250. The trigger 150, the cam 250, the needle 140, and the sheath 190 may be operatively connected such that when the trigger 150 is actuated, the cam 250 moves, and the needle 140 and the sheath 190 move according to the movement of cam 250. In the examples of FIGS. 6A-6C, it is shown that actuating the trigger 150 in a first direction (as indicated by arrow 152a in FIG. 6A) operatively moves the cam 250 in one or more of a second direction (indicated by arrow 252a in FIG. 6B) and a third direction (indicated by arrow 252b in FIG. 6B). The second direction 252a may be a translational direction and the third direction 252b may be a rotational direction. The cam 250 may have a cylindrical shape and may include a track that has one or more straight portions 254a and a curved portion 254b. The track of the cam 250 allows the cam 250 and the sheath 190 attached to the cam 250 to move in the second direction 252a and the third direction 252b, or a combination thereof via engagement of a pin of the suture passer with the track of cam 250. The pin may be attached to the handle portion 120 and engagement of the pin with the track of the cam 250 limits movement of the cam 250 to the track of cam 250.

FIG. 6C shows movement of a sheath 190 that corresponds to movement of the cam 250 shown in FIG. 6B. The movement of the cam 250 (as indicated by arrow 252a in FIG. 6B) causes the sheath 190 of FIG. 6C to move distally with the needle 140 towards the distal portion 170 of the suture passer 100, as indicated by arrow 252a in FIG. 6C. During a portion of the distal movement of the sheath 190 and the needle 140, the sheath 190 may simultaneously rotate about and relative to the needle 140. The sheath 190 may be configured to rotate in a same direction (for example, the third direction 252b) as the cam 250 moves towards the distal portion 170 (in the second direction 252a). The track of the cam 250 may be ramped and stepped so that a pin connected to the handle 120 may follow the track of the cam 250 and progress along the track by falling onto a next portion of the track.

Actuation of the trigger 150 in the first direction 152a may cause the cam 250 to move such that the sheath 190 rotates by a pre-determined amount of degrees for every complete actuation of the trigger 150. The sheath 190 rotates in a same rotational direction for each actuation of the trigger 150. The pre-determined amount may be at least 45 degrees or at least 90 degrees. The pre-determined amount may be at most 270 degrees or at most 180 degrees. The pre-determined amount may be 45-270 degrees or 90-180 degrees.

The ferrule 180 may be retained in the distal portion of the suture passer (as shown in FIG. 4C) and unmounted from the needle 140 (as shown in FIG. 4D) by actuating the trigger 150 in the first direction 152a. Release of the actuation of the trigger 150 may translate the needle 140 away from the retained ferrule 180 towards the hollow tube (such as hollow tub 160) of the suture passer. Subsequent actuation of the trigger 150 in the first direction moves the needle 140 towards the distal portion of the suture passer to re-insert the needle 140 within the ferrule 180, release the ferrule 180 from the distal portion of the suture passer via movement of the sheath 190 relative to the needle 140, and mount the ferrule 180 back on the needle 140, as described previously in reference to FIG. 5. Release of the subsequent actuation of the trigger 150 may move the needle 140 and the ferrule 180 mounted on the needle 140 away from the distal portion 170 towards the hollow tube 160 of the suture passer.

Figure 7A:
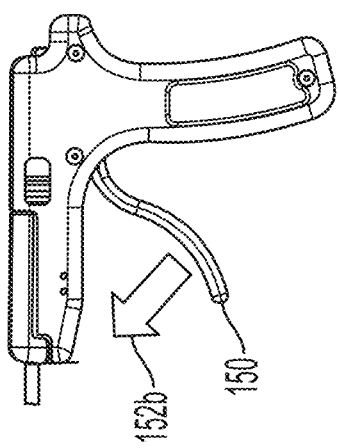
FIGS. 7A-7C show an exemplary schematics that illustrate a progression for passing a ferrule to the distal portion of the suture passer.
Figure 7C:
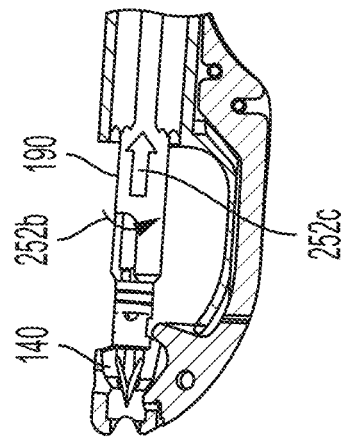
Figure 7B:
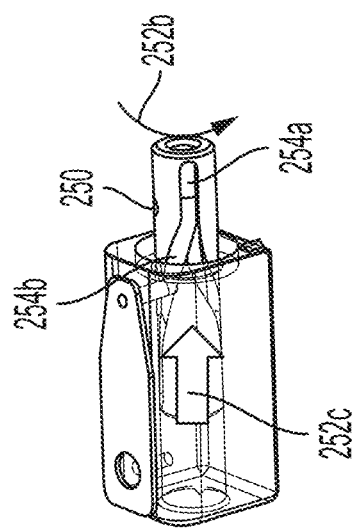

FIGS. 7A-7C show examples of the retrieval of the ferrule 180 from the distal portion 170 of the suture passer 100. In the examples of FIGS. 7A-7C, actuating the trigger 150 in a direction indicated by arrow 152b (which a direction opposite to the first direction indicated by arrow 152a in FIG. 6A) may move the cam 250 in one or more of a fourth direction (indicated by arrow 252c in FIG. 7B) and the third direction (indicated by arrow 252b in FIG. 7B). Actuation of the trigger 150 in the direction indicated by arrow 152b may include releasing the actuation of the trigger in the first direction. The fourth direction 252c may be a direction opposite to the direction indicated by arrow 252a in FIG. 6B. The fourth direction 252c may be a translational direction and the third direction 252b may be a rotational direction. The rotational direction 252b of the cam 250 during passing of the ferrule 180 (as shown in FIGS. 6A-6C) may be the same rotational direction 252b during retrieving of the ferrule 180 (as shown in FIGS. 7A-7C).

FIG. 7C shows movement of a sheath 190 that corresponds to movement of the cam 250 shown in FIG. 7B. In the examples of FIGS. 7B and 7C, movement of the cam 250 in the fourth direction 252c causes the sheath 190 to translate with the needle 140 in a proximal direction away from the distal portion 170 of the suture passer 100. During a portion of the translational movement of the sheath 190 and the needle 140 away from the distal portion 170, the sheath 190 may simultaneously rotate about and relative to the needle 140. The sheath 190 may be configured to rotate in a same direction (for example, the direction as indicated by arrow 252b) as the cam moves away from the distal portion 170 (in the direction indicated by arrow 252c).

The suture passer may include an arm that has an actuating surface located proximally of the distal portion of the suture passer so that the suture passer may be configured to retrieve a ferrule based on actuation of the actuating surface located proximally to the distal portion. FIG. 8 shows an example of a suture passer 300 that includes an arm 340 having an actuatable engagement 320 and an actuating surface 330. The actuatable engagement 320 may be biased in an upward direction with respect to the orientation of the device in FIG. 8 to snap into a recess 321 of the ferrule 380 for retaining the ferrule 380 in the distal portion 310. The position of the actuatable engagement 320 in recess 321 shown in FIG. 8 is a latched position of the actuatable engagement 320. The actuating surface 330 may be located in a hollow tube 360 of the suture passer 300. Having the actuating surface of the arm 340 positioned in the hollow tube 360 can prevent jamming during retrieval of the ferrule 380 due to tissue interfering with the actuating surface 330 or other parts of the distal portion during release of the ferrule 380. The suture passer 300 may include a sheath 390 that includes an actuating surface 345 configured to interface the actuating surface 330 of the arm 340 for moving the actuatable engagement 320 from the latched position to an unlatched position in which the actuatable engagement 320 is snapped out of the recess 321 of the ferrule 380. The sheath 390 may move relative to the needle 385 to position the actuating surface 345 of the sheath 390 so that it pushes the actuating surface 330 of the arm in a first direction (as indicated by arrow 320a in FIG. 8). The movement of the sheath 390 relative to the needle may be a translational movement. As the actuating surface 330 of the arm 340 moves in the first direction 320a, the proximal portion 342 of the arm 340 pivots (counterclockwise in the view of FIG. 8) about pin 343, which causes a body 350 of the arm 340 to move proximally (as indicated by arrow 320c in FIG. 8), which in turn, causes the actuatable engagement 320 of the arm 340 to move in a second direction (as indicated by arrow 320b in FIG. 8). The arm 340 may comprise a living hinge 355 for moving the actuatable engagement 320 from the latched position to an unlatched position.

Moving the actuatable engagement 320 to the unlatched position releases the ferrule 380 from a distal portion 310. The ferrule 380 may be mounted to the needle 385 as the actuatable engagement 320 moves to the unlatched position. The ferrule 380 may be mounted to the needle 385 after the actuatable engagement 320 moves to the unlatched position. The ferrule 380 may be mounted to the needle 385 via a friction fit between the ferrule 380 and the needle 385 or by snapping one or tabs of the ferrule 380 into one or more recesses of the ferrule 380 (as discussed in reference to FIG. 9A-9C). After the actuatable engagement 320 is in the unlatched positioned and the ferrule 380 is mounted to the needle 385, the mounted ferrule 380 may be moved from the distal portion 310 of the suture passer towards the proximal portion 360 of the suture passer via translational movement of the needle 385.

Movement of the needle within the ferrule during retrieval of the ferrule from the distal portion may unlatch the ferrule from the distal portion and simultaneously securely mount the ferrule to the needle. The ferrule may be securely mounted to the translatable needle via a friction fit or via actuation of one or more tabs of the ferrule. FIG. 9A show a cross-sectional view of an exemplary ferrule 400. Ferrule 400 may include an interior portion 402 configured for receiving a needle 420 (such as needle 140), one or more tabs 410 configured for retaining the ferrule 400 to the needle 420, and an aperture 411 configured for receiving an actuatable engagement (such as actuatable engagement 220, 320) of a suture passer (such as suture passer 100, 300). The one or more tabs 410 may include an exterior surface configured to interface with a sheath 430.

FIGS. 9B-9D show example positions of the one or more tabs 410 based on positioning of the needle 420 in the ferrule 400 and the sheath 430 over the ferrule 400. For example, should the ferrule 400 be retained in a distal portion of a suture passer by an actuatable engagement snapped into the aperture 411 (as shown in FIG. 4), distal movement of the needle 420 towards the ferrule 400 via actuation of a trigger (such as trigger 150) of a suture passer inserts the needle 420 within the interior portion 402 of the ferrule 400. The sheath 430 may move with the needle 420 towards the ferrule 400. During movement of the needle 420 and the sheath 430 towards the ferrule 400, the needle 420 may extend further distally than the sheath 430. As shown in the example of FIG. 9B, during a first portion of the movement of the needle 420 within the ferrule 400 (as indicated by arrow 404a), the one or more tabs 410 of the ferrule 400 may be positioned over a first exterior surface 440 of the needle 420. The first exterior surface 440 may push the one or more tabs 410 of the ferrule 400 away from the interior portion 402 of the ferrule 400 as indicated by arrow 412a. As shown in the example of FIG. 9C, during a second portion of the movement of the needle 420 within the ferrule 400, the one or more tabs 410 of the ferrule 400 may be positioned over one or more recesses 450 defined by a second exterior surface 460 recessed from the first exterior surface 440. As shown in the examples of FIGS. 9C and 9D, the recess 450 may be configured to receive at least a portion of the one or more tabs 410.

The one or more tabs 410 of the ferrule 400 may be configured to interface with the sheath 430. For example, when the needle 420 is inserted into the ferrule 400 to a position in which the one or more tabs 410 of the ferrule 400 are positioned over the recess 450, the sheath 430 may be translatable (as indicated by arrow 432a) relative to the needle 420 over an exterior surface 470 of the one or more tabs 410 based on user actuation of a trigger of the suture passer. The sheath 430 positioned over the one or more tabs 410 pushes the one or more tabs 410 to deflect towards the recess 450 of the needle 420 (as indicated by arrow 412b). As the sheath 430 interfaces with the exterior surface 470 of the one or more tabs 410, the one or more tabs 410 are held in a deflected or pressed position for holding the one or more tabs 410 within the recess 450. In this way, the ferrule 400 is held securely against the needle 420. Upon release of user actuation of a trigger or actuation of a second trigger of the suture passer, the sheath 430 may be retracted away from the ferrule to no longer interface the exterior surface 470 of the one or more tabs 410. When the sheath 430 no longer interfaces the exterior surface 470 of the one or more tabs 410, the one or more tabs 410 will no longer be held in the pressed position for the holding the one or more tabs 410 pressed within the recess 450 of the needle 420, thus the ferrule 400 will no longer be securely held against the needle 420. The relative movement of the sheath 430 may include one or more of a translational movement or a rotational movement.

The suture passer may include a first trigger for translating the needle to and from the distal portion and for passing a ferrule to the distal portion during translation of the needle to the distal portion. The suture passer may include a second trigger for retrieving the ferrule from the distal portion and mounting the ferrule onto the needle. FIGS. 10A-10D show an example of a suture passer 500. The suture passer 500 may include a first trigger 502 and a second trigger 504. The suture passer 500 may include a handle portion 506 and a shaft 508 that includes a tissue engaging recess 510. FIGS. 10A-10D also show zoomed-in schematics of the tissue engaging recess 510. The first trigger 502 and the second trigger 504 may be operatively connected to each other in the handle portion 506. Similar to suture passer 100 and suture passer 300, suture passer 500 may include a translatable needle 509 configured to extend from a proximal portion 511a of the tissue engaging recess 510 to a distal portion 511b of the tissue engaging recess 510. Similar to suture passer 300, suture passer 500 may include a ferrule 520 and a sheath 530. The sheath 530 may at least partially cover one or more tabs (such as one or more tabs 410) of the ferrule 520 during one or more portions of the ferrule passing and retrieval process. When the sheath 530 at least partially covers the ferrule 520, the sheath 530 presses the one or more tabs of the ferrule 520 to extend towards a recess (such as recess 450) of the needle 509 for retaining the ferrule 520 onto the needle 509.

The second trigger may be operatively connected to the needle and the sheath via followers of a cam. For example, the handle portion 506 may include a first pin 505a of the sheath 530 and a second pin 505b of the needle 509. The second pin 505b may be attached to a base 513 of the needle 509. The handle portion 506 may include a spring 542 connected to the base 513 and a spring 544 connected to the first pin 505a. The spring 542 urges the base 513 and the second pin 505b on the base 513 in a direction away from the distal portion 501. The spring 544 urges the first pin 505a in a direction away from the distal portion 501 along a base track 546 of base 513. The first pin 505a may be configured to follow a first track 507a of a translatable cam 503 and the second pin 505b may be configured to follow a second track 507b of the translatable cam 503. The translatable cam 503 is connected to the second trigger 504 and operatively connected to the first trigger 502.

FIGS. 10A-10D show positions of a ferrule 520 (such as ferrule 400) based on distal movement of a needle 509 towards a distal portion 501 of the suture passer. The movement of the needle 509, and thus the position of the ferrule 520 mounted on the needle 509 may be based on a position of one or more of the first trigger 502, the second trigger 504, and a trigger lock 535. Actuation of the first trigger 502 may cause the first pin 505a of the sheath 530 to move along the first track 507a and the second pin 505b of the needle 509 to move along the second track 507b. Actuation of the first trigger 502 connected to the base 513 of the needle 509, moves pin 505b positioned on the base 513 towards the distal portion 501 of the suture passer 500 against the bias of the spring 542. As the pin 505b moves distally towards the distal portion 501, pin 505b pushes cam 503 such that cam 503 pivots counterclockwise with respect to the orientation of FIG. 10A. The counterclockwise pivot of cam 503 pushes pin 505a distally against the bias of spring 544 in the base track 546. As the pins 505a, 505b move distally, the cam 503 tracks the pins 505a, 505b along their respective tracks 507a, 507b. As the pins 505a, 505b are moved to different positions along their respective tracks 507a, 507b, a spacing between the first pin 505a and the second pin 505b may change and control relative movement of the sheath 530 and the needle 509.

Figure 10A:
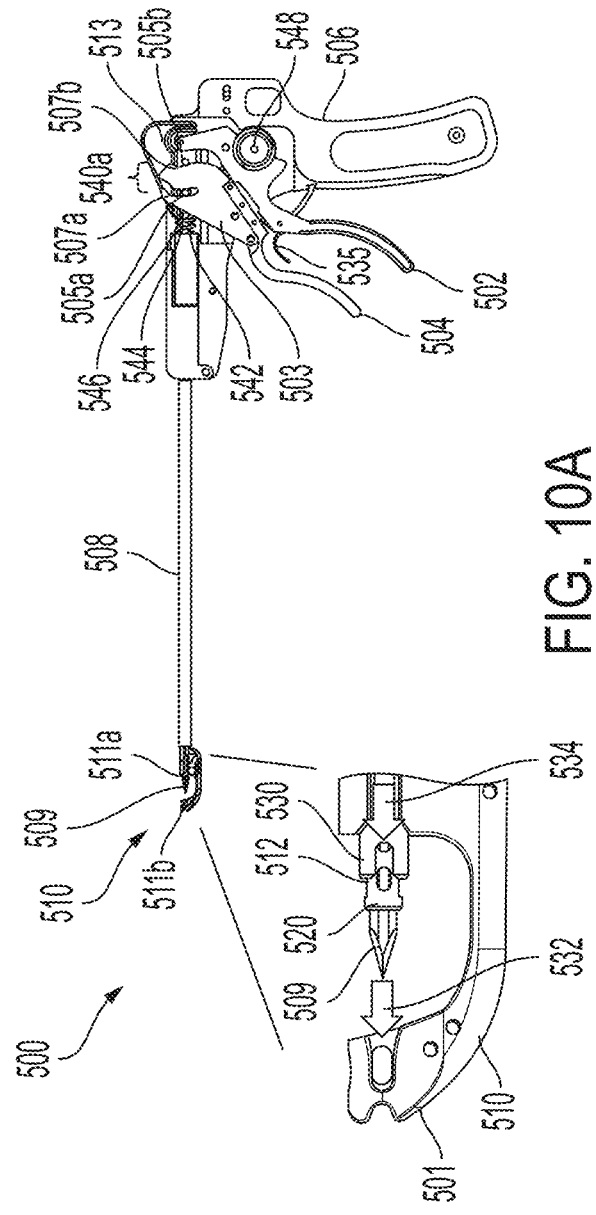
FIGS. 10A-10D show an exemplary progression for passing a ferrule to a distal portion of the suture passer.

In the example of FIG. 10A, the ferrule 520 mounted on the needle 509 moves (as indicated by arrow 532) towards a distal portion 501 of the suture passer 500 based on a first portion of a user actuation of the first trigger 502. The first trigger 502 may be actuated by a user pulling on the first trigger 502 such that the first trigger 502 pivots counterclockwise with respect to the orientation of FIG. 10A about pivot 548. During the first portion of the actuation of the first trigger 502, the first pin 505a of the sheath 530 and the second pin 505b of the needle 509 may be spaced apart by a first distance 540a and may move simultaneously along their respective tracks 507a, 507b. The simultaneous movement of the pins 505a, 505b causes the needle 509 (and the ferrule 520 mounted to the needle 509) and the sheath 530 to move together to the distal end 501. During movement of the needle 509, the ferrule 520 mounted to the needle, and the sheath 530 to the distal portion 501, the ferrule 520 is at least partially covered by a sheath 530 (such as sheath 430). When the sheath 530 at least partially covers the ferrule 520, the sheath 530 presses the one or more tabs 512 of the ferrule 520 to extend towards a recess (such as recess 450) of the needle 509 for retaining the ferrule 520 to the needle 509. The sheath 530 may move with the ferrule 520 and the needle 530 towards the distal portion 501 of the suture passer 500 as indicated by arrow 534. Upon completion of the first portion of the actuation of the first trigger 502, the first trigger 502 may be positioned about half way through a full range of motion of the first trigger 502.

Figure 10B:
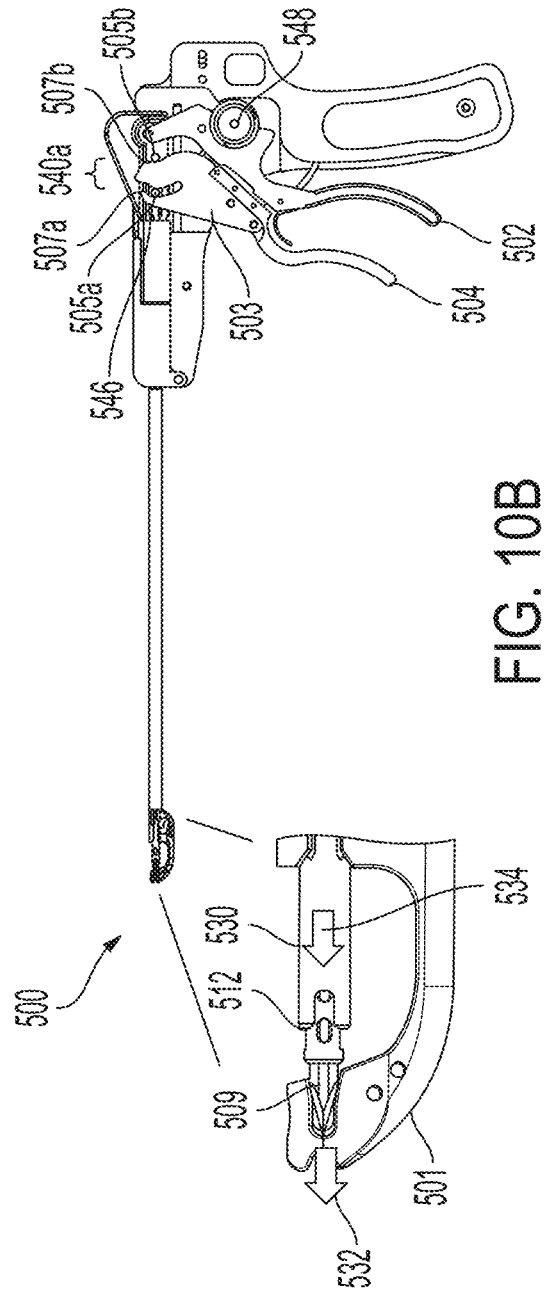

FIG. 10B shows an example of a second portion of the user actuation of the first trigger 502. The second portion of the actuation may be further actuation of the first trigger 502 in a same direction as the first portion of the actuation. During, the second portion of the actuation of the first trigger 502, the first pin 505a and the second pin 505b may be spaced the first distance apart and move simultaneously along their respective tracks 507a, 507b. In the example of FIG. 10B, ferrule 520 mounted on the needle 509 and at least partially covered by the sheath 530 is located closer to the distal portion 501 of the suture passer compared to FIG.

10A. For example, as shown in FIG. 10B, the needle 509 is inserted in the distal portion 501 and the sheath 530 continues to at least partially cover the ferrule 520. The sheath 530 may at least partially cover one or more tabs (such as one or more tabs 410) of the ferrule 520 for retaining the ferrule 520 onto the needle 509. Upon completion of the second portion of the actuation of the first trigger 502, the first trigger 502 may be positioned about two-thirds of the way through its full range of motion. After the second portion of the user actuation of the first trigger 502, further actuation in the same direction as the second portion may change a distance between the first pin 505a and the second pin 505b.

Figure 10C:
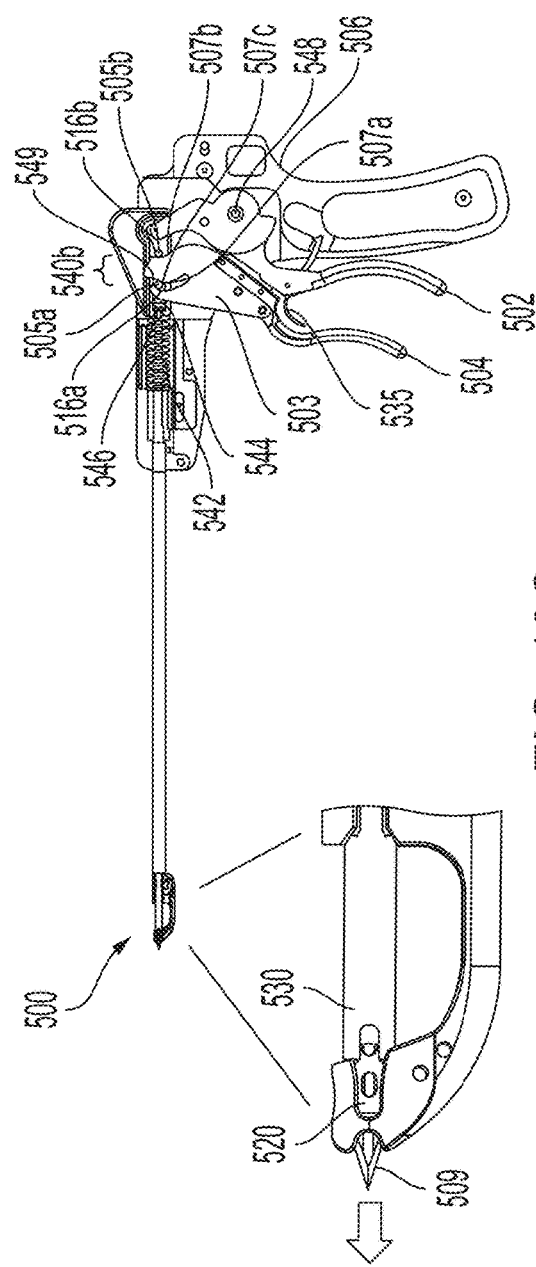
Figure 10D:
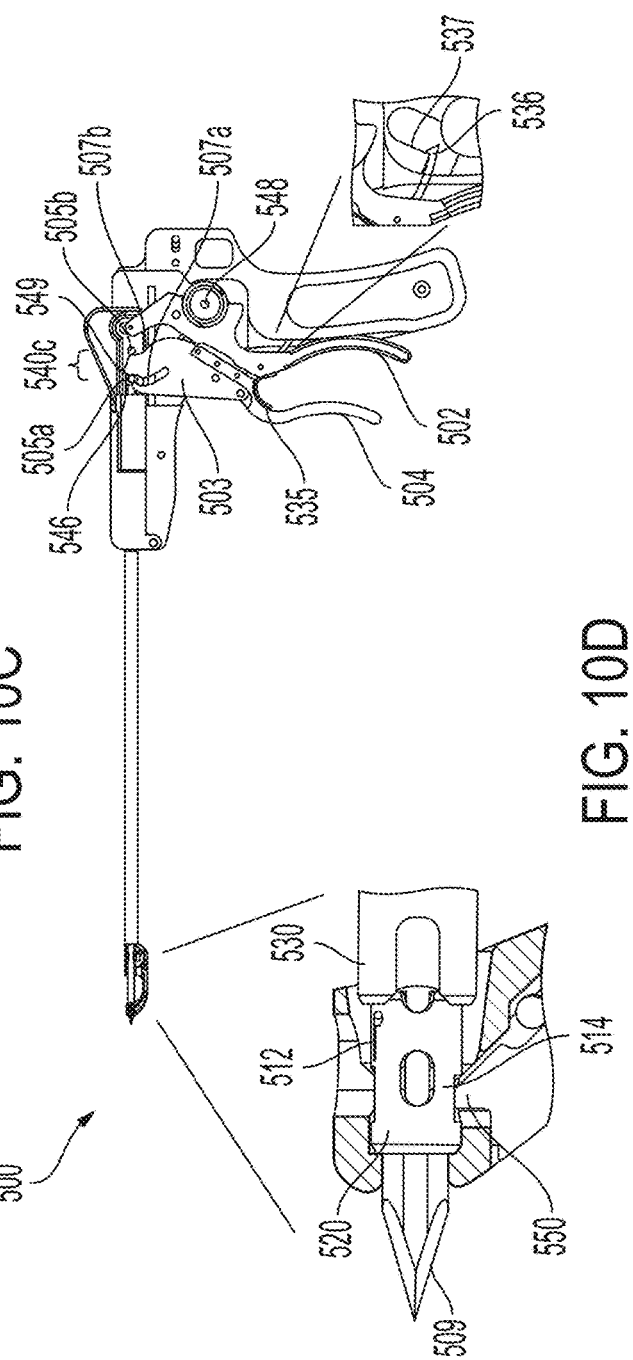

FIG. 10C shows an example of a third portion of the user actuation of the first trigger 502. The third portion of the actuation may be further actuation of the first trigger 502 in a same direction as the second portion of the actuation. During, the third portion of the actuation of the first trigger 502, the first pin 505a of the sheath 530 and the second pin 505b of the needle 509 may be spaced an intermediate distance 540b apart and move simultaneously along their respective tracks 507a, 507b. The intermediate distance 540b may be a transition between the first distance 540a and a second distance 540c. The pins 505a, 505b are spaced the intermediate distance between each other when the pins 505a, 505b are respectively positioned at locations 516a, 516b of cam 203. Movement of the pins 505a, 505b respectively along the track 507a, 507b of the cam 503 for spacing the pins 505a and 505b the intermediate distance 540b apart may initiate movement of the needle 509 and the ferrule 520 mounted to the needle 509 to move (as indicated by the arrow in FIG. 10C) relative to the sheath 530 to a distal-most position of the needle 509. Upon completion of the third portion of the actuation of the first trigger 502, the first trigger 502 may be positioned about three-quarters of the way through its full range of motion and the needle 509 and the ferrule 520 mounted to the needle 509 have initiated movement (as indicated by the arrow in FIG. 10C) relative to the sheath to the distal-most position of the needle 509. In FIG. 10D, the needle 509 is in its distal-most position.

FIG. 10D shows an example of a fourth portion of the user actuation of the first trigger 502. The fourth portion of the actuation may be further actuation of the first trigger 502 in the same direction as the third portion of the actuation. During the fourth portion of the actuation of the first trigger 502, the first pin 505a of the sheath 530 and the second pin 505b of the needle 509 may move simultaneously along their respective tracks 507a, 507b from positions 516a, 516b to positions in which the pins 505a, 505b are spaced the second distance 540c apart. The second distance 540c may be at most the first distance 540a.

Movement of the needle 509 relative to the sheath 530 is due to curvature of tracks 507a, 507b. For example, as the base 513 connected to the first trigger 502 moves with the fourth portion of the actuation of the first trigger 502, the pin 505b positioned on the base 513 moves with the base 513 towards the distal portion 501. The pin 505b pushes against track 507b of the cam 503 to pivot the cam 503 counterclockwise (with respect to the orientation of FIGS. 10C and 10D) and track the pin 505b. The track 507a of cam 503 is curved to form a recess 549 such that as the cam 503 pivots counterclockwise, the track 507a tracks around pin 505a via the recess 549 and pushes against the pin 505a to move the pin 505a distally against the bias of spring 544. As shown in the example of FIG. 10D, the recess 549 may be recessed away from the distal portion 501 from a surface 507c of track 507a. As the pin 505b of the needle 509 moves towards the distal portion 501 at a first rate, the recess 549 allows the pin 505a of the sheath 530 to move towards the distal portion 501 at a second rate that is slower than the first rate. In this way, the needle 509 moves distally with the pin 505b of the needle 509 at the first rate, while the sheath 530 and the pin of the sheath 505a move distally at the second rate during the fourth portion of actuation of the first trigger 502. This relative movement causes the needle 509 to move such that the sheath 530 no longer at least partially covers the ferrule 520 to press the one or more tabs 512 (such as one or more tabs 410) of the ferrule 520 towards a recess (such as recess 450) of the needle 509. When the one or more tabs 512 of the ferrule 520 are no longer pressed by the sheath 530 to extend towards the recess of the needle 509, the ferrule 520 is no longer securely mounted to the needle 509.

With the needle 509 in its distal-most position as shown in FIG. 10D, the ferrule 520 is retained in the distal portion 501 via an actuatable engagement 550 (such as actuatable engagement 220, 320) biased in an upward direction with respected to the orientation of FIG. 10D. The bias of the actuatable engagement 550 moves the actuatable engagement 550 to snap into an aperture 514 (such as aperture 411) of the ferrule 520 and in this position, the actuation engagement 550 retains the ferrule 520 in the distal portion 501. Upon completion of the fourth portion of the actuation of the first trigger 502, the first trigger 502 is positioned at a far end of its full range of motion, the ferrule 520 is retained in the distal portion 501, and the sheath 530 uncovers one or more tabs 512 of the ferrule 520.

In the example of FIG. 10D, the first trigger 502 is shown in a pressed position (at a far end of its full range of motion). The suture passer 500 may include the trigger lock 535 for holding the first trigger 502 in the pressed position. FIG. 10C shows an example of the trigger lock 535 in an unlocked position and the right inset of FIG. 10D shows an example of the trigger lock 535 in a locked position. The handle portion 506 may include a track 537 for guiding movement of the trigger lock 535 and the trigger lock 535 may include a hook 536 for latching onto the track 537. The first trigger 502 may remain in the pressed position unless the second trigger 504 is actuated or the trigger lock 535 is manually moved to an unlocked position by a user.

Movement of trigger lock 535 to an unlock position (for example, as shown in FIG. 10C) releases the first trigger 502 from its pressed position. With the first trigger 502 released, the base 513 and the pin 505b on the base 513 move away from the distal portion 501 under force of the spring 542 and the pin 505a of the sheath 530 move away from the distal portion 501 under the force of the spring 544. Movement of pin 505a of the sheath 530 away from the distal portion 501 pushes against track 507a of cam 503 which causes cam 503 to pivot clockwise with respect to the orientation of FIG. 10D. The pivoting cam 503 tracks the pins 505a, 505b. Since the ferrule 520 is retained in the distal portion 501 by actuatable engagement 550, the movement of the pins 505a, 505b translates the needle 509 and the sheath 530 together away from the distal portion 501.

To initiate retrieval of the ferrule 520 retained in the distal portion 501, the first trigger 502 can be actuated again by a user to move the needle 509 and the sheath 530 back to the distal portion 501. This actuation repeats translation movements of the needle 509 and the sheath 530 as shown in FIGS. 10A-10D except that the ferrule 520 is retained in the distal portion 501 and is not mounted on the needle 509. Full actuation of the first trigger 502 to its pressed position moves the needle 509 and the sheath 530 to the distal portion 501 so that the needle 509 is fully inserted into the distal portion 501 in a distal-most position of the needle. The first trigger 502 in its pressed position is locked into the pressed position by trigger lock 535.

After the first trigger 502 has been locked in the pressed position and the needle 509 is in its distal-most position (as shown by the needle position of FIG. 10D), the second trigger 504 may be pressed by a user which moves the trigger lock 535 to an unlocked position and releases the first trigger 502 from its pressed position. The actuation of the second trigger 504 may move the sheath 530 relative to the needle 509 for releasing the ferrule 520 from the distal portion 501 and mounting the ferrule 520 the needle 509. Movement of the sheath 530 relative to the needle 509 causes the sheath to press one or more tabs 512 of the ferrule 520 into a recess (such as 450) of the needle 509 for securing the ferrule 520 to the needle 509 and move the actuatable engagement 550 against the bias from a latched position (shown in FIG. 10D) to an unlatched position for releasing the ferrule 520 from the distal portion 501. Actuation of the second trigger 504 moves the sheath 530 relative to the needle 509 to secure the ferrule 520 to the needle 509 as the sheath 530 moves the actuatable engagement 550 against the bias to release the ferrule 520 from the distal portion 501.

Figure 10E:
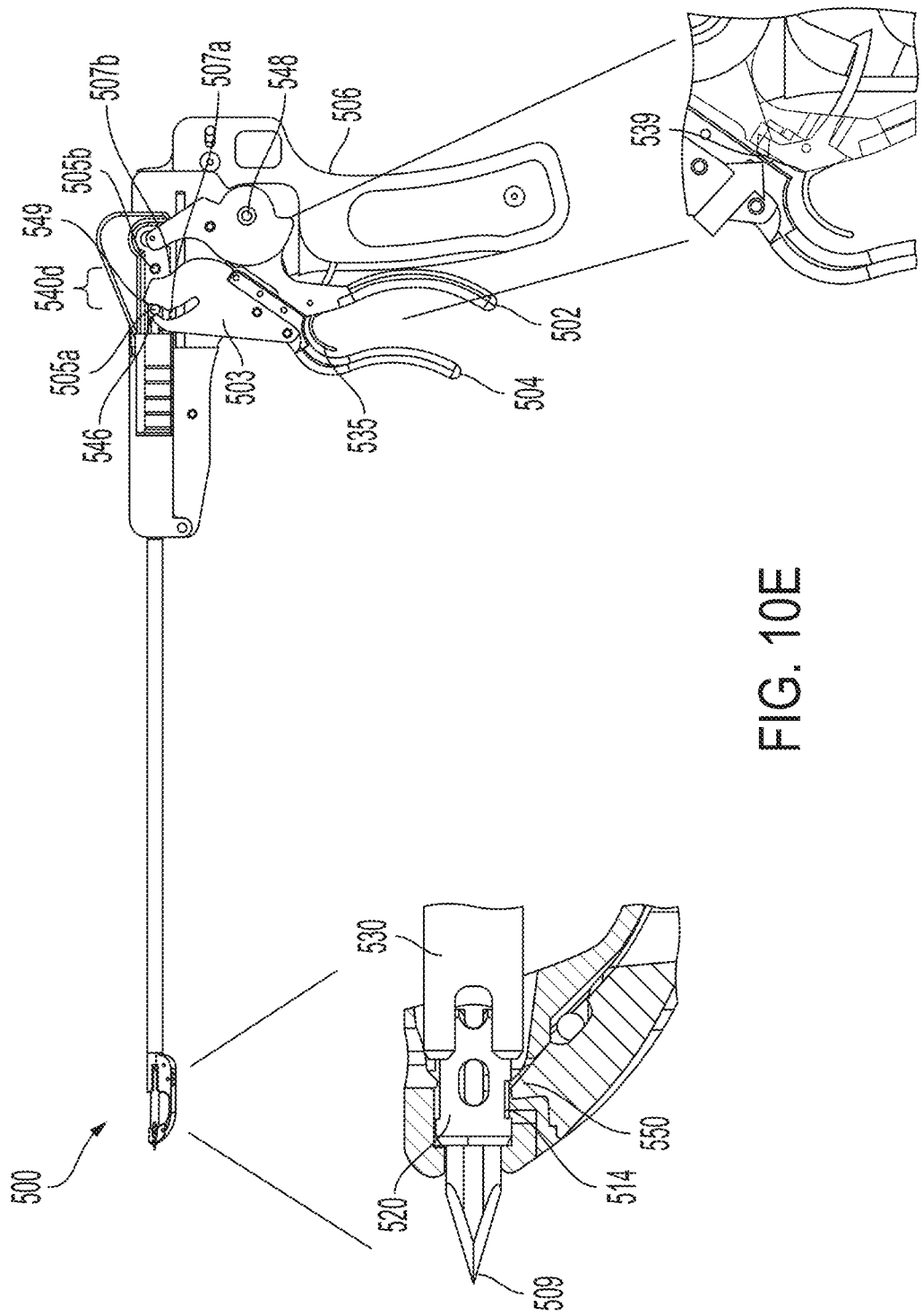
FIG. 10E shows an example of user actuation of a second trigger when a first trigger is in a pressed position.

FIG. 10E shows an example of user actuation of the second trigger 504 when the first trigger 502 is in the pressed position. During user actuation of the second trigger 504, the second pin 505b of the needle 509 remains stationary while the first pin 505a of the sheath 530 is pushed by the translatable cam 503 connected to the second trigger 504 towards the distal portion 501 of the suture passer 500. This movement of the translatable cam 503 spaces the track 507b of the cam 503 away from the second pin 505b of the needle 509. The second pin 505b is connected to the needle 509, and since the second trigger 504 does not move the second pin 505b, the second pin 505b and the needle 509 remain stationary. The first pin 505a is connected to the sheath 530, and therefore, movement of the first pin 505a moves the sheath 530. Upon actuation of the second trigger 504, the translatable cam 503 connected to the second trigger 504 pivots counterclockwise with respect to the orientation of FIG. 10E such that it pushes the first pin 505a towards the distal portion 501 of the suture passer 500. Specifically, the translatable cam 503 pushes the first pin 505a against the bias of spring 544 (shown in FIG. 10C) that urges the first pin 505a away from the distal portion 501 along the track 546. The movement of the first pin 505a towards the distal portion 501 may space the first pin 505a of the sheath 530 and the second pin 505b of the needle 509 a third distance 540d apart. The third distance 540d may equal the first distance 540a.

Actuation of the second trigger 504 moves the sheath 530 relative to the needle 509, which results in the sheath 530 covering the one or more tabs 512 (as shown in the left inset of FIG. 10E) of the ferrule 520 to hold the ferrule 520 against the needle 509. Movement of the sheath 530 relative to the needle 509 to a distal-most position of the sheath 530 (sheath position in FIG. 10E) in the distal portion 501 causes the sheath 530 to cover at least a portion of aperture 514 of the ferrule 520 and move the actuatable engagement 550 against its bias and release the ferrule 520 from the distal portion 501. The sheath 530 may move the actuatable engagement 500 via proximal actuation as described in reference to FIG. 8. The inset of FIG. 10E shows the actuatable engagement 550 pushed into an unlatched position due to positioning of the sheath 530 as described in reference to FIG. 8.

Figure 10F:
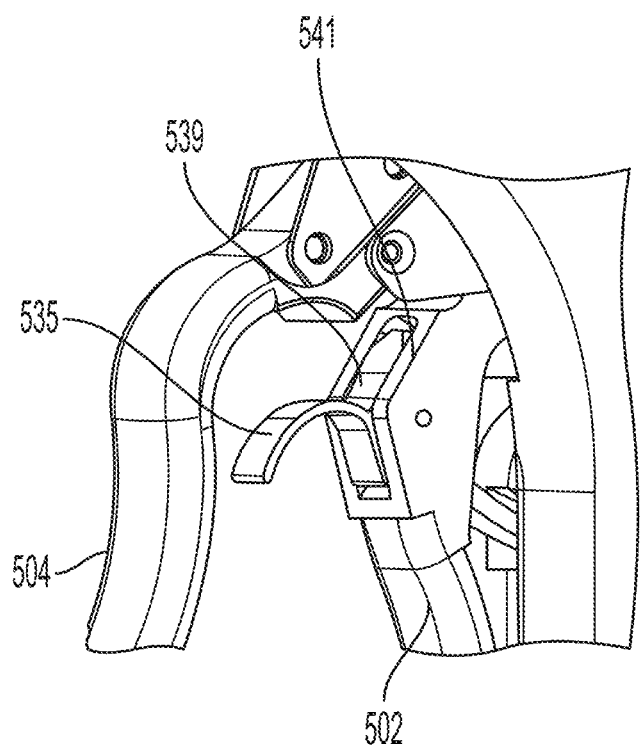
FIG. 10F shows an example of a trigger lock of a suture passer in an unlocked position.

Actuation of the second trigger 504 by the user moves the trigger lock 535 from a locked position to an unlocked positions. The right inset of FIG. 10E shows a zoomed-in image of the trigger lock 535 in a locked position. For illustrative purposes, the first trigger 502 is shown as transparent. Actuation of the second trigger 504 in the direction of the arrow of the right inset of FIG. 10E causes the second trigger 504 to pivot counterclockwise (with respect to the orientation of FIG. 10E) and press against a lever 539 of the trigger lock 535. Pressing lever 539 moves the trigger lock 535 to an unlocked position. FIG. 10F shows an example of the trigger lock 535 in an unlocked position.

Upon release of the second trigger 504 by the user, the needle 509, the ferrule 520 mounted to the needle 509, and the sheath 530 move together away from the distal portion 501 under force of the bias of the spring 542 and the spring 544. The spring 544 urges pin 505a away from the distal portion 501 and the spring 542 urges the needle base 513 (and the pin 505b on the needle base 513) away from the distal portion 501. As the pins 505a, 505b move away from the distal portion 501, the pin 505a pushes the cam 503 connected to the second trigger 504 to pivot clockwise (with respect to the orientation of FIG. 10E) and upon sufficient clockwise rotation, the track 507b of the cam 503 contacts the pin 505b. Once the track 507b contacts the pin 505b, the pins 505a, 505b are positioned as shown in FIG. 10B and spaced the first distance 540a apart.

As the second trigger 504 is released by the user, pins 505a, 505b move simultaneously, while maintaining the first distance 540d (540a) apart. For example, the pins 505a, 505b can move from the position shown in FIG. 10E to the position shown in FIG. 10B to the position shown in FIG. 10A. In FIGS. 10A, 10B, and 10E, the pins 505a, 505b are spaced at the first distance 540d (540a) away from each other allowing the sheath 530 to cover a portion of the ferrule 520. Therefore, the pins 505a and 505b are spaced the first distance apart and the sheath 530 covers the portion of the ferrule 520 throughout release of the second trigger 504.

During the release of the second trigger 504, pressure maintained on the second trigger 504 by the user prevents the second trigger 504 from reaching its maximum clockwise rotation. When the second trigger 504 is prevented by the user from reaching its maximum clockwise rotation, the second trigger 504 maintains pressure on the first trigger 502 which keeps the pins 505a, 505b spaced apart at the first distance 540d (540a) as the second trigger 504 is released. The second trigger 504 can maintain pressure on the first trigger 502 by pressing on surface 541 (shown in FIG. 10F) of the first trigger 502.

FIG. 11 shows a schematic illustrating exemplary positions of the sheath 530 and a needle 509 in the tissue engaging region 510 of suture passer 500 (as shown in FIGS. 10A-10D) based on user actuation of the first trigger 502 and the second trigger 504. The exemplary positions of FIG. 11 are associated with passing the ferrule 520 to a distal portion of the suture passer 500 and retrieving the ferrule from the distal portion 501 of the suture passer 500.

In the example of FIG. 11, step A, schematically illustrates that the needle 509 and the sheath 530 are positioned in the proximal portion 511a of the tissue engaging region 510 and the ferrule 520 is positioned and retained in the distal portion 511b of the tissue engaging region 510. The proximal portion 511a may include a hollow tube (such as hollow tube 160) in which the needle 509 is translatably mounted. As the first trigger 502 is actuated, the needle 509 and the sheath 530 extending about the needle 509 move towards the ferrule 520 in the distal portion 511*b*.

At step B, the needle 509 has moved to distal-most position of the distal portion 511*b* in which the needle is inserted into ferrule 520 in the distal portion 511*b* of the tissue engaging region 510. On the other hand, at step B, the sheath 530 has moved to a proximal position of the distal portion 511*b*. At step B, a second trigger 504 may be actuated for moving the sheath 530 relative to the needle 509 from the proximal position of the distal portion 511*b* in a direction towards the distal-most position of the distal portion 511*b*. The movement of the sheath 530 relative to the needle 509 may be configured to release the ferrule 520 from the actuatable engagement 550 in the distal portion 511*b* and securely mount the ferrule 520 to the needle 509. The ferrule 520 may be mounted to the needle 509 via movement described in FIGS. 9B-9D and FIG. 10E.

At step C, the needle 509 and sheath 530 are in a position for releasing the ferrule 520 from the actuatable engagement 550 in the distal portion 501 and mounting the ferrule 520 securely to the needle 509. The first trigger 502 and the second trigger 504 may be released so that the sheath 530 moves with the needle 509 away from the distal portion 511*b* towards the proximal portion 511*a* of the tissue engaging region 510.

At step D, the needle 509 and the sheath 530 are positioned in the proximal portion 511*a* of the tissue engaging region 510 and the ferrule 520 is mounted to the needle 509.

At step E, the needle 509 and the ferrule 520 mounted to the needle 509 are positioned in the distal end of the distal portion 511*b* and the sheath 530 is positioned in the proximal end of the distal portion 511*b*. In transitioning from step E to step F, the needle 509 and the ferrule 520 mounted to the needle 509 move relative to the sheath 530. At step F, the ferrule 520 may be retained in the distal portion 511*b* and unmounted from the needle 509. Steps D-F may be steps of movements described in FIGS. 10A-10D.

Between steps A and B, steps C and D, and steps D and E, the sheath 530 may cover at least a portion of the ferrule 520 and lock the ferrule 520 to the needle as described in FIGS. 9B-9D.

The suture holder may be the needle tip of the needle. FIGS. 12A-12B show an exemplary suture holder that is a needle tip 600 of a needle 610. The needle 610 may include a needle shaft 620 configured to extend about an external surface of the needle tip 600 so that the needle shaft 620 may receive the needle tip 600. The needle 610 may be used in suture passers such as suture passer 100, 300, 500. The needle tip 600 may be configured to hold suture as described above in reference to the ferrule 180, 400, 520. As shown in FIG. 14A, the needle 610 includes a hollow needle shaft 620 and the needle tip 600 is configured to removably attach to the hollow needle shaft 620 via engagement of an internal surface 630 of the needle shaft 620 with an outer surface 640 of the needle tip 600. For example, the internal surface 630 of the needle shaft 620 may include an inwardly extending portion 650 configured to extend into a recess 660 of the needle tip 600 to secure the needle tip 600 to the needle shaft 620. The recess 660 may be recessed from the outer surface 640 of the needle tip 600.

The needle tip 600 may include an aperture 670 configured for receiving an actuatable engagement 680 (such as actuatable engagement 220, 320) of the suture passer. As described in reference to ferrules 180, 400, 520 the needle tip 600 may be retained in the distal portion 602 when the actuatable engagement 680 (such as actuatable engagement 220, 320) of the suture passer is snapped into a latched position with the aperture 670 and the needle tip 600 may be released from the distal portion 602 when the actuatable engagement 680 is pushed away from the latched position to an unlatched position with the aperture 670 by a sheath 690. The sheath 690 may push the actuatable engagement 680 from the latched position to the unlatched position based on movement of the sheath 690 relative to the needle shaft 620. As the actuatable engagement 680 moves from the latched position with the aperture 670 to an unlatched position with the aperture 670, the needle tip 600 is released from the distal portion 602 and mounted to the needle shaft 620.

FIG. 12B shows the exemplary needle tip 600 detached from the needle shaft 620. The needle tip 600 may be detached from the needle shaft 620 when the actuatable engagement 680 is in the latched position for retaining the needle tip 600 in the distal portion 602.

A distal portion 604 of the needle tip 600 and a distal portion 692 of the needle shaft 620 are configured to pierce through tissue to create a hole. A size of the hole created may be based on a size of the distal portion 604 of the needle tip 600 and a size of the distal portion 692 of the needle shaft 620. The distal portion 692 of the needle shaft 620 may be configured to create a hole having a larger size than a hole created by the distal portion 604 of the needle tip 600. The larger size hole created by the needle shaft 620 eases movement of the needle tip 600 through tissue during passing of the needle tip 600 to the distal portion 602 and during retrieval of the needle tip 600 from the distal portion 602.

Figure 12C:
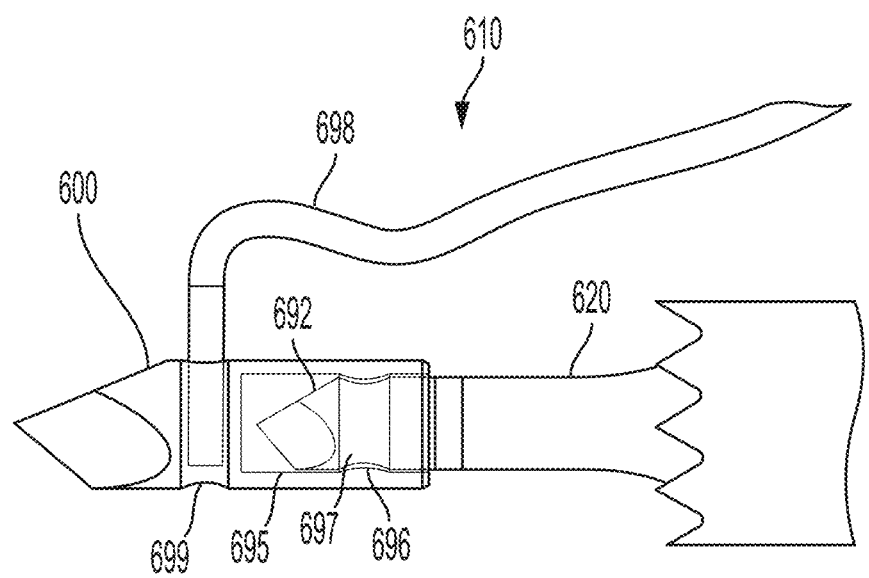
FIG. 12C shows an exemplary suture holder that forms a needle tip and includes a counterbore for receiving a distal end of the needle shaft.

FIG. 12C shows a variation in which the distal portion 692 of the needle shaft 620 fits within a counterbore 695 of the needle tip 600. The counterbore 695 may include a ridge 696 that fits into a groove 697 of the counterbore 695 to retain the needle tip 600 on the distal portion 692 of the needle shaft 620. FIG. 12C also illustrates the suture 698 loaded into a bore 699 of the needle tip 600.

Figure 13:
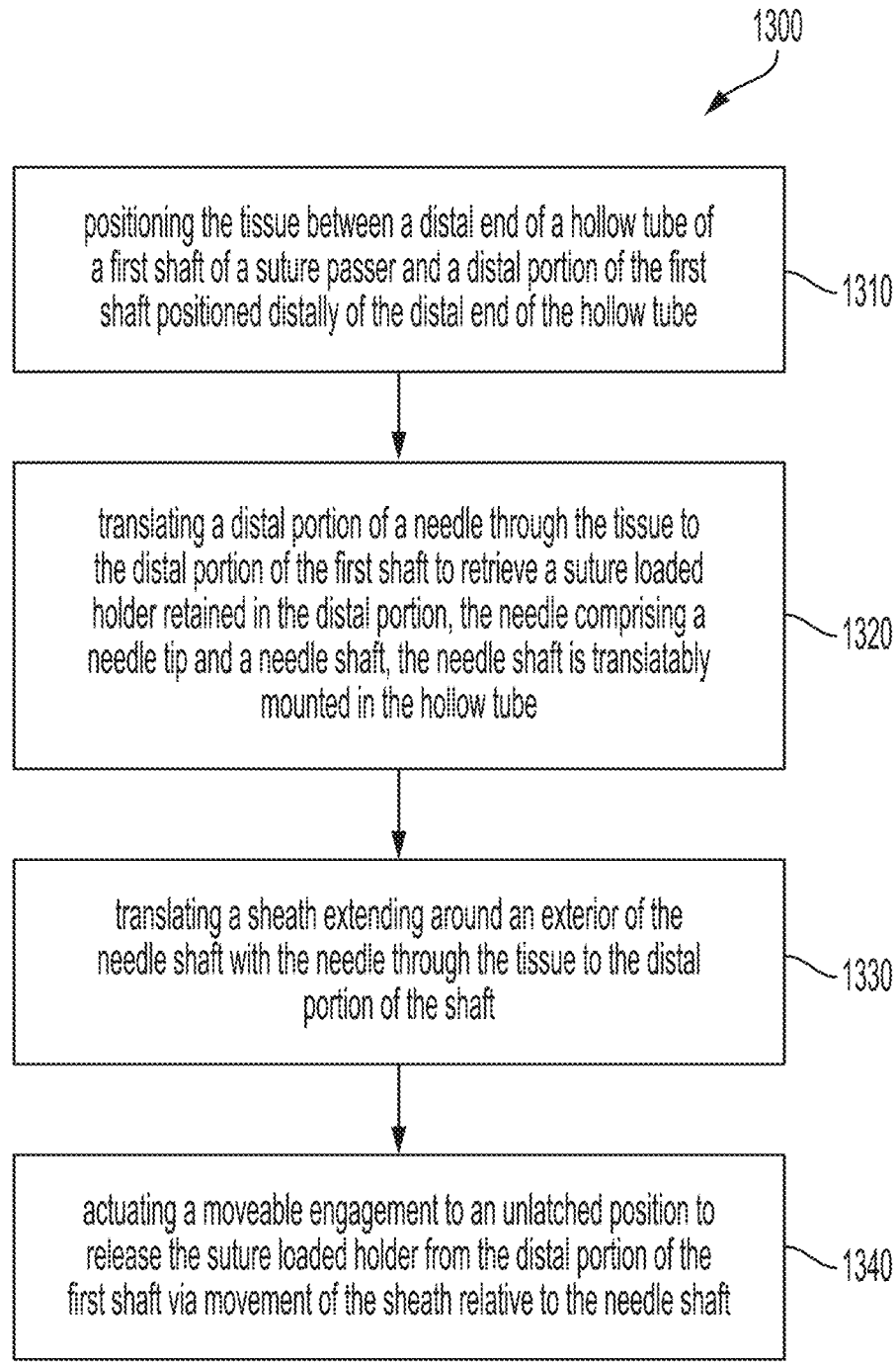
FIG. 13 shows a flowchart of an exemplary method for passing a suture through tissue.

FIG. 13 shows a flowchart of an exemplary method 1300 for passing a suture through tissue. The method 1300 may be used to suture tissue with suture passer 100, 300, 500 as described above. The method 1300 may include steps 1310, 1320, 1330, and 1340. At step 1310, tissue may be positioned between a distal end of a hollow tube of a first shaft of a suture passer and a distal portion of the first shaft positioned distally of the distal end of the hollow tube. At step 1320, a distal portion of a needle may be translated through the tissue to the distal portion of the first shaft to retrieve a suture loaded holder retained in the distal portion. The needle may include a needle tip and a needle shaft and the needle shaft may be translatably mounted in the hollow tube. At step 1330, a sheath extending around an exterior of the needle shaft may be translated with the needle through the tissue to the distal portion of the shaft. At step 1340, a moveable engagement may be actuated to an unlatched position to release the suture loaded holder from the distal portion of the first shaft via movement of the sheath relative to the needle shaft.

The foregoing description, for the purpose of explanation, has been described with reference to specific examples. However, the illustrative discussions above are not intended to be exhaustive or to limit the invention to the precise forms disclosed. Many modifications and variations are possible in view of the above teachings. The examples were chosen and described in order to best explain the principles of the techniques and their practical applications. Others skilled in the art are thereby enabled to best utilize the techniques and various examples with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of the patents and publications referred to in this application are hereby incorporated herein by reference.

The invention claimed is:

1. A suture passer, comprising:
a first shaft comprising a hollow tube and a distal portion located distally of a distal end of the hollow tube;
a needle comprising a needle tip and a needle shaft translatably mounted in the hollow tube and having a distal portion that is extendable out of the distal end of the hollow tube for passing a suture loaded holder through tissue positioned between the distal end of the hollow tube and the distal portion of the first shaft via a stroke of the needle;
an actuatable engagement located in the distal portion of the first shaft for retaining the suture loaded holder in the distal portion of the first shaft after the suture loaded holder has passed through the tissue; and
a sheath extending around an exterior of the needle shaft and translatable with the needle shaft for at least a portion of a stroke of the needle shaft, wherein the sheath is moveable relative to the needle shaft for actuating the actuatable engagement to an unlatched position to release the suture loaded holder from the distal portion of the first shaft, wherein relative movement of the sheath to the needle shaft comprises a translational movement of the sheath along a longitudinal axis of the needle shaft.

2. The suture passer of claim 1, wherein relative movement of the sheath to the needle shaft comprises a rotational movement of the sheath about a longitudinal axis of the needle shaft.

3. The suture passer of claim 1, wherein the actuatable engagement is configured to be moved to a latched position by the suture loaded holder when the suture loaded holder is moved into the distal portion via the stroke of the needle.

4. The suture passer of claim 1, comprising an arm that comprises the actuatable engagement at the distal portion of the first shaft and an actuating surface positioned proximal to the actuatable engagement.

5. The suture passer of claim 4, wherein the sheath is configured to actuate the actuatable engagement by interfacing with the actuating surface, and when the sheath interfaces the actuating surface via relative movement to the needle shaft, the actuatable engagement is pushed away from the suture loaded holder from the latched position to an unlatched position.

6. The suture passer of claim 5, wherein as the sheath moves to actuate the actuatable engagement to the unlatched position, the suture loaded holder is released from the distal portion and securely mounted to the needle shaft via movement of the one or more tabs of the suture loaded holder towards a recess of the needle shaft by the sheath.

7. The suture passer of claim 4, wherein the actuating surface of the arm is positioned in the distal portion of the first shaft.

8. The suture passer of claim 4, wherein the actuating surface of the arm is positioned proximally of the distal portion.

9. The suture passer of claim 1, wherein the suture loaded holder is a ferrule.

10. The suture passer of claim 1, comprising a first trigger operatively connected to the sheath and the needle shaft, wherein pressing the first trigger causes the sheath to translate together with the needle shaft to the distal portion of the first shaft, and wherein releasing the pressed first trigger causes the sheath to translate together with the needle shaft away from the distal portion of the first shaft.

11. The suture passer of claim 10, wherein movement of the first trigger in a first direction causes the sheath to translate together with the needle shaft to the distal portion, and after or as the sheath and the needle shaft translate to the distal portion, the sheath is configured to rotate in a rotational direction about the needle shaft and movement of the first trigger in a second direction causes the sheath to translate together with the needle shaft away from the distal portion and after or as the sheath and the needle shaft translate away from the distal portion, the sheath is configured to rotate about the needle shaft in the rotational direction.

12. The suture passer of claim 10, comprising a second trigger configured to move the sheath relative to the needle shaft to actuate the actuatable engagement to an unlatched position and press one or more tabs of the suture loaded holder into a recess of the needle for securing the suture loaded holder to the needle shaft, and movement of the second trigger causes the first trigger to move to a pressed position.

13. The suture passer of claim 12, wherein the first trigger and the second trigger are operatively connected to the sheath and the needle shaft via a cam comprising a first track for a first follower attached to the sheath and a second track for a second follower attached to the needle.

14. The suture passer of claim 13, wherein movement of the first trigger causes the first follower and the second follower to move simultaneously, and movement of the second trigger subsequent to movement of the first trigger causes the first follower to move relative to the second follower.

15. The suture passer of claim 1, further comprising a jaw extending around the sheath, wherein the jaw is configured to translate with the needle and grip the tissue positioned between the distal end of the hollow tube and the distal portion of the first shaft.

16. The suture passer of claim 1, wherein the distal portion of the first shaft further comprises one or more apertures configured to prevent tissue from jamming the distal portion.

17. The suture passer of claim 1, wherein the distal portion of the first shaft further comprises an inner surface configured to interface with an outer surface of the needle to prevent tissue from jamming the distal portion.

18. The suture passer of claim 1, wherein the distal portion of the first shaft further comprises a proximal end having a tapered inner perimeter configured to prevent tissue from jamming the distal portion.

19. The suture passer of claim 1, wherein the actuatable engagement moves laterally to the unlatched position relative to a longitudinal axis of the sheath.

20. A method for passing a suture through tissue, comprising:
positioning the tissue between a distal end of a hollow tube of a first shaft of a suture passer and a distal portion of the first shaft positioned distally of the distal end of the hollow tube;
translating a distal portion of a needle through the tissue to the distal portion of the first shaft to retrieve a suture loaded holder retained in the distal portion, the needle comprising a needle tip and a needle shaft, the needle shaft is translatably mounted in the hollow tube;

translating a sheath extending around an exterior of the needle shaft with the needle through the tissue to the distal portion of the first shaft;

actuating a moveable engagement to an unlatched position to release the suture loaded holder from the distal portion of the first shaft via movement of the sheath relative to the needle shaft, wherein movement of the sheath relative to the needle shaft comprises translating the sheath along a longitudinal axis of the needle shaft.

21. The method of claim 20, wherein movement of the sheath relative to the needle shaft comprises rotating the sheath about a longitudinal axis of the needle shaft.

22. The method of claim 20, wherein the suture passer comprises an arm that comprises the moveable engagement at the distal portion of the first shaft and an actuating surface positioned proximal to the moveable engagement, wherein the sheath engages the actuating surface to actuate the moveable engagement.

23. The method of claim 22, wherein actuating the moveable engagement to release the suture loaded holder from the distal portion of the first shaft comprises interfacing the sheath with the actuating surface via relative movement to the needle shaft, and pushing away the moveable engagement from the suture loaded holder from a latched position to the unlatched position.

24. The method of claim 23, wherein as the sheath moves to actuate the actuatable engagement to the unlatched position, the suture loaded holder is released from the distal portion and securely mounted to the needle shaft via movement of one or more tabs of the suture loaded holder towards a recess of the needle shaft by the sheath.

25. The method of claim 22, wherein the actuating surface of the arm is positioned in the distal portion of the first shaft.

26. The method of claim 22, wherein the actuating surface of the arm is positioned proximally of the distal portion.

27. The method of claim 20, comprising interfacing an inner portion of the suture loaded holder with the needle shaft for mounting the suture loaded holder onto the needle shaft via a friction fit or interfacing an inner portion of the needle shaft having one or more movable tabs configured to move into a slot of the needle shaft for mounting the suture loaded holder onto the needle shaft, and securing the suture loaded holder in the distal position of the first shaft so that the suture loaded holder can be unmounted from the needle shaft when the moveable engagement is in a latched position positioned.

28. The method of claim 27, comprising pressing a first trigger when the suture loaded holder is mounted on the needle shaft to move the suture loaded holder with the needle via translation of the needle to the distal portion of the first shaft, the first trigger being operatively connected to the sheath and needle.

29. The method of claim 20, comprising pressing a first trigger operatively connected to the sheath and the needle to translate the sheath with the needle through the tissue to the distal portion of the first shaft, and the method comprises releasing the pressed first trigger to translate the sheath together with the needle away from the distal portion of the first shaft.

30. The method of claim 29, comprising moving the first trigger in a first direction to translate the sheath together with the needle shaft to the distal portion, moving the first trigger in a second direction to translate the sheath together with the needle shaft away from the distal portion of the first shaft, and rotating the sheath in a rotational direction about the needle shaft after or as the sheath and the needle shaft translate to and from the distal portion.

31. The method of claim 30, comprising moving a second trigger to a pressed positioned to actuate the moveable engagement to rotate the sheath in the rotational direction about the needle shaft.

32. The method of claim 31, wherein the first trigger and the second trigger are operatively connected to the sheath and the needle via a cam comprising a first track for a first follower attached to the sheath and a second track for a second follower attached to the needle.

33. The method of claim 32, wherein moving the first trigger causes the first follower and the second follower to move simultaneously, and moving the second trigger subsequent to moving of the first trigger causes the first follower to move relative to the second follower.

34. The method of claim 20, comprising:

repositioning the tissue between the distal end of the hollow tube of the first shaft of the suture passer and the distal portion of the first shaft positioned distally of the distal end of the hollow tube;

translating the distal portion of the needle shaft mounted in the hollow tube and the suture loaded holder mounted on the needle through the tissue to the distal portion of the first shaft;

translating once again the sheath with the needle shaft through the tissue to the distal portion of the first shaft; and actuating the moveable engagement positioned in the distal portion of the first shaft for retaining the suture loaded holder in a latched position in the distal portion of the first shaft.

35. A suture passer, comprising:

a first shaft comprising a hollow tube and a distal portion located distally of a distal end of the hollow tube;

a needle comprising a needle tip and a needle shaft translatably mounted in the hollow tube and having a distal portion that is extendable out of the distal end of the hollow tube for passing a suture loaded holder through tissue positioned between the distal end of the hollow tube and the distal portion of the first shaft via a stroke of the needle;

an actuatable engagement located in the distal portion of the first shaft for retaining the suture loaded holder in the distal portion of the first shaft after the suture loaded holder has passed through the tissue, wherein the actuatable engagement is configured to be moved to a latched position by the suture loaded holder when the suture loaded holder is moved into the distal portion via the stroke of the needle; and a sheath extending around an exterior of the needle shaft and translatable with the needle shaft for at least a portion of a stroke of the needle shaft, wherein the sheath is moveable relative to the needle shaft for actuating the engagement to an unlatched position to release the suture loaded holder from the distal portion of the first shaft.

36. The suture passer of claim 35, wherein relative movement of the sheath to the needle shaft comprises a rotational movement of the sheath about a longitudinal axis of the needle shaft.

37. The suture passer of claim 35, wherein relative movement of the sheath to the needle shaft comprises a translational movement of the sheath along a longitudinal axis of the needle shaft.

38. The suture passer of claim 35, comprising an arm that comprises the actuatable engagement at the distal portion of the first shaft and an actuating surface positioned proximal to the actuatable engagement.

39. The suture passer of claim 35, wherein the suture loaded holder is a ferrule.

40. The suture passer of claim 35, comprising a first trigger operatively connected to the sheath and the needle shaft, wherein pressing the first trigger causes the sheath to translate together with the needle shaft to the distal portion of the first shaft, and wherein releasing the pressed first trigger causes the sheath to translate together with the needle shaft away from the distal portion of the first shaft.

41. A suture passer, comprising:
- a first shaft comprising a hollow tube and a distal portion located distally of a distal end of the hollow tube;
- a needle comprising a needle tip removably attached to a needle shaft, wherein the needle tip is configured to hold a suture, and wherein the needle is translatably mounted in the hollow tube and has a distal portion that is extendable out of the distal end of the hollow tube for passing the needle tip through tissue positioned between the distal end of the hollow tube and the distal portion of the first shaft via a stroke of the needle;
- an actuatable engagement located in the distal portion of the first shaft for retaining the needle tip in the distal portion of the first shaft after the needle tip has passed through the tissue; and
- a sheath extending around an exterior of the needle shaft and translatable with the needle shaft for at least a portion of a stroke of the needle shaft, wherein the sheath is moveable relative to the needle shaft for actuating the engagement to an unlatched position to release the needle tip from the distal portion of the first shaft.

42. The suture passer of claim 41, wherein the needle tip comprises an outer surface configured to engage with an inner surface of the needle shaft.

43. The suture passer of claim 41, wherein the needle tip comprises an aperture configured to receive the actuatable engagement.

44. The suture passer of claim 41, wherein the needle tip is configured to detach from the needle shaft when the actuatable engagement is actuated to a latched position.

45. The suture passer of claim 41, wherein a distal portion of the needle shaft has a diameter that is larger than a diameter of a distal portion of the needle tip.

46. The suture passer of claim 41, wherein the needle tip comprises a counterbore, and a distal portion of the needle shaft is configured to fit into the counterbore.

* * * * *